United States Patent [19]

Blewett et al.

[11] Patent Number: 5,993,447

[45] Date of Patent: Nov. 30, 1999

[54] APPARATUS FOR THERMAL TREATMENT OF TISSUE

[75] Inventors: Jeffrey J. Blewett, Plantsville; Christopher W. Maurer; Corbett W. Stone, both of Newtown, all of Conn.

[73] Assignee: United States Surgical, Norwalk, Conn.

[21] Appl. No.: 08/699,091

[22] Filed: Aug. 16, 1996

[51] Int. Cl.⁶ .................................................. A61B 17/39
[52] U.S. Cl. ............................ 606/50; 607/101; 606/41; 600/105
[58] Field of Search .......................... 606/41, 42, 45–50; 128/642; 607/100–105, 122; 600/104, 105, 374

[56] References Cited

U.S. PATENT DOCUMENTS

| | | | |
|---|---|---|---|
| 5,109,830 | 5/1992 | Cho | 606/7 |
| 5,370,675 | 12/1994 | Edwards et al. | 607/101 |
| 5,403,311 | 4/1995 | Abele et al. | 606/49 |
| 5,449,356 | 9/1995 | Walbrink et al. | 606/49 |
| 5,472,441 | 12/1995 | Edwards et al. | 606/41 |
| 5,514,131 | 5/1996 | Edwards et al. | 606/45 |
| 5,536,267 | 7/1996 | Edwards et al. | 607/101 |

FOREIGN PATENT DOCUMENTS

| | | |
|---|---|---|
| 9513027 | 5/1995 | WIPO . |
| 9706857 | 2/1997 | WIPO . |

OTHER PUBLICATIONS

Olinger et al, "Eighteen–Gauge . . . Research Application", Surgical Neurology, vol. 2, pp. 151–159, May 1974.

Olinger et al., "Eighteen–Gauge Microscopic–Telescopic Needle Endoscope with Electrode Channel: Potential Clinical and Research Application", *Surgical Neurology*, May 1974, pp. 151–159.

*Primary Examiner*—Michael Peffley

[57] ABSTRACT

An auxiliary electromagnetic thermal treatment apparatus for use with an endoscope to provide the endoscope with electromagnetic thermal treatment capabilities is provided. The auxiliary apparatus includes a handle portion and an elongate portion connected to the handle portion and dimensioned to be at least partially inserted within a working channel of an endoscope. The elongate portion includes at least one delivery tube having a memory portion comprised of a shape memory material and defining a normally unstressed curved configuration. The one delivery tube is longitudinally moveable relative to the handle portion to extend the memory portion beyond the working channel of the endoscope such that the memory portion assumes the normal unstressed curved configuration thereof. An electromagnetic probe is disposed within the delivery tube and is longitudinally moveable relative to the delivery tube to extend a probe end portion thereof beyond the delivery tube and within tissue. The electromagnetic probe is adapted to follow the curved configuration of the memory portion of the delivery tube for deployment at an angularly oriented relation with respect to the endoscope. A first actuator is mounted to the handle portion and operatively connected to the delivery tube. A second actuator is also mounted to the handle portion and is operatively connected to the electromagnetic probe. The actuator is moveable to extend the probe end portion beyond the delivery tube. The present disclosure is also directed to a combination of an endoscope and an auxiliary thermal treatment device. A method for thermally treating tissue is also disclosed.

32 Claims, 23 Drawing Sheets

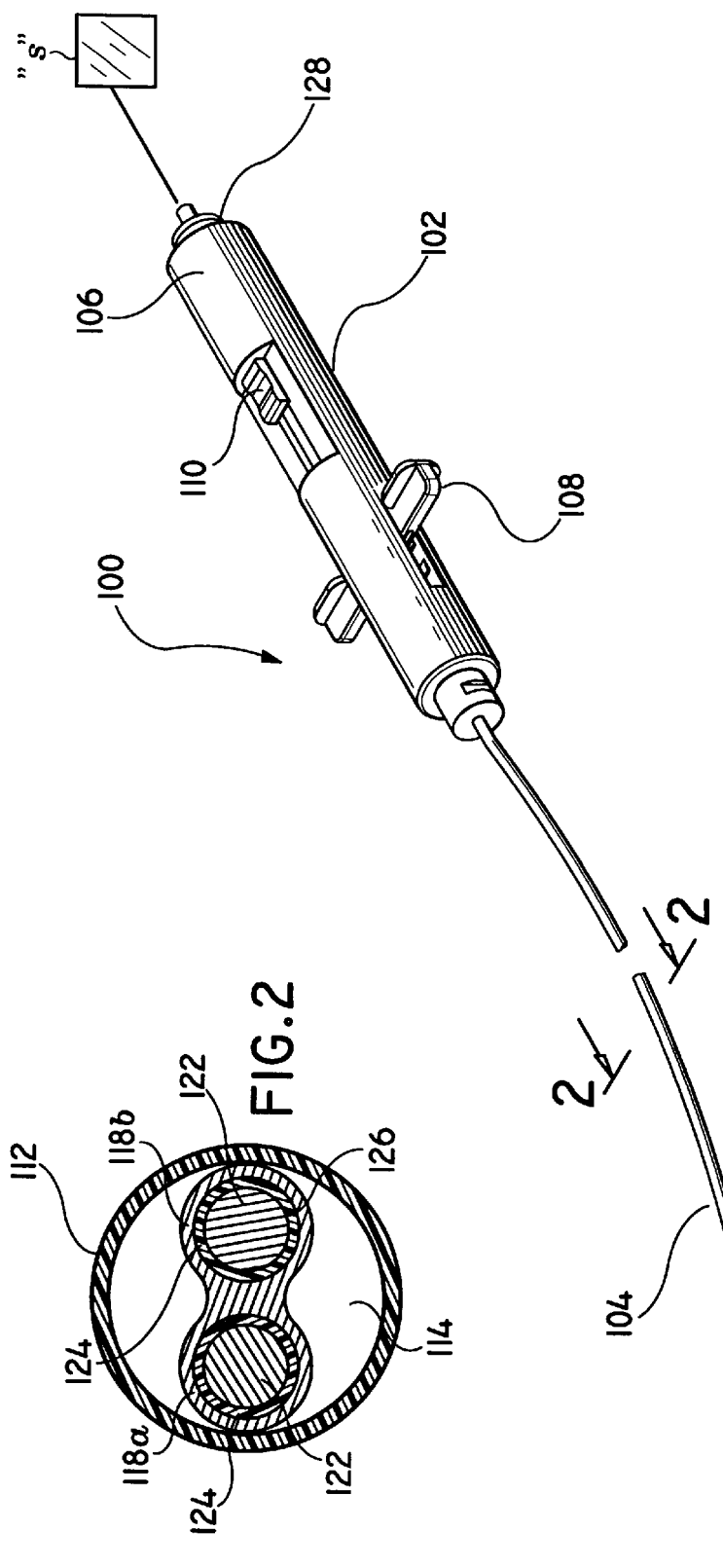

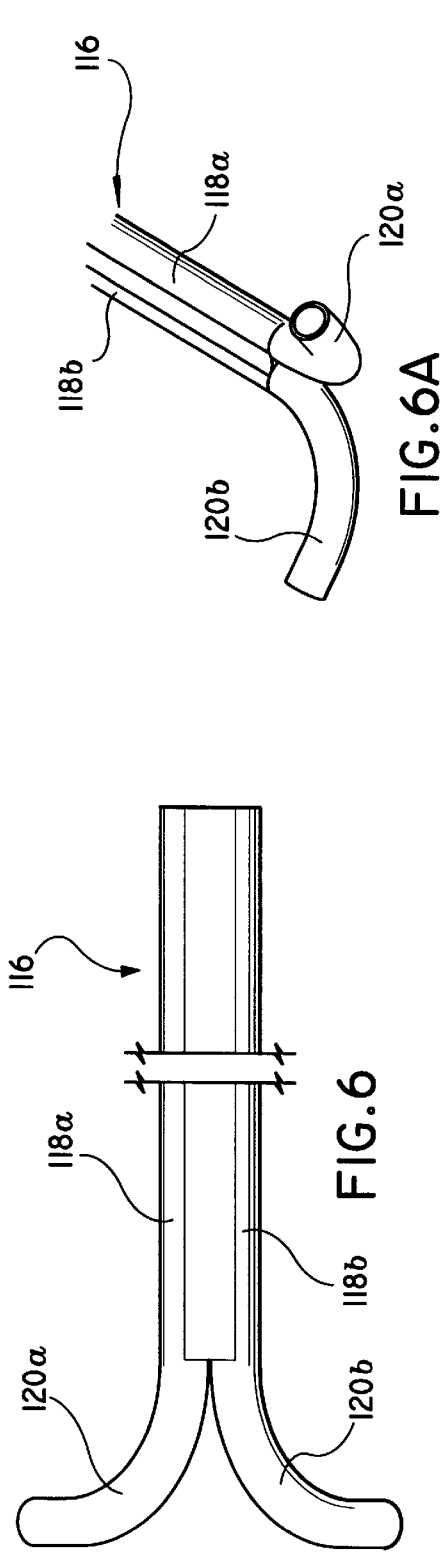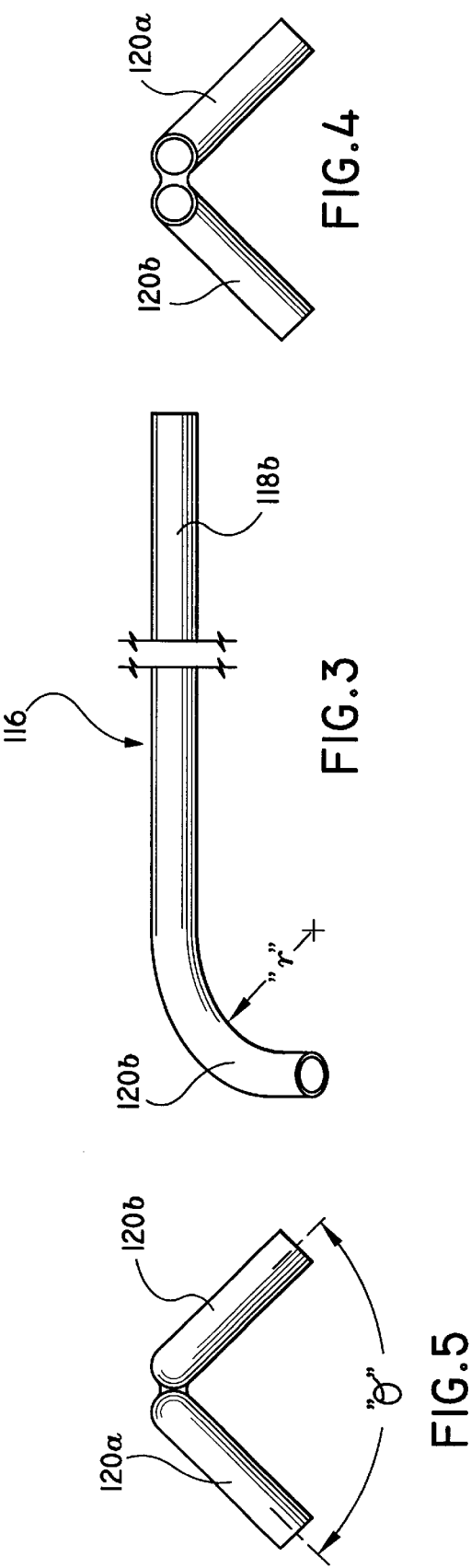

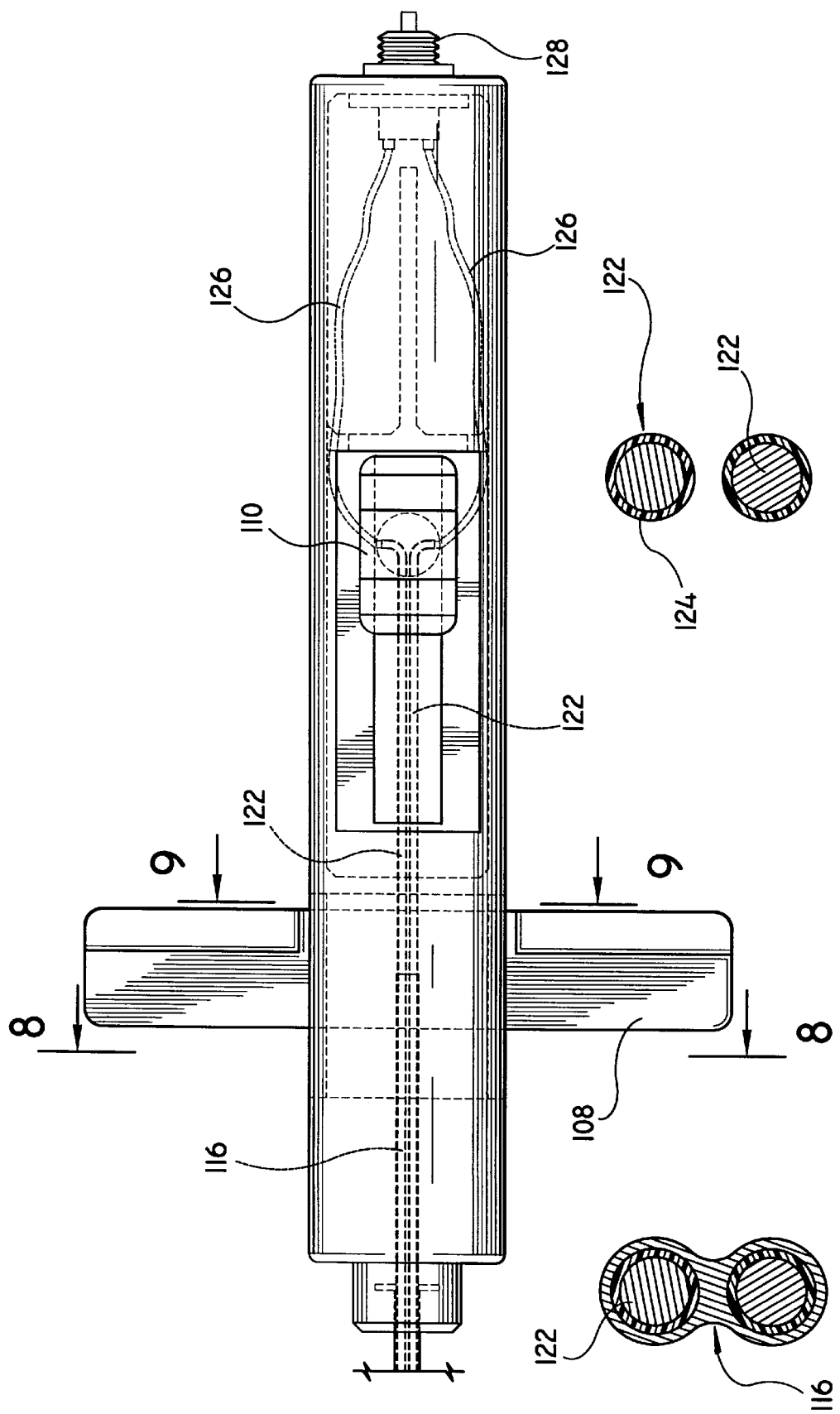

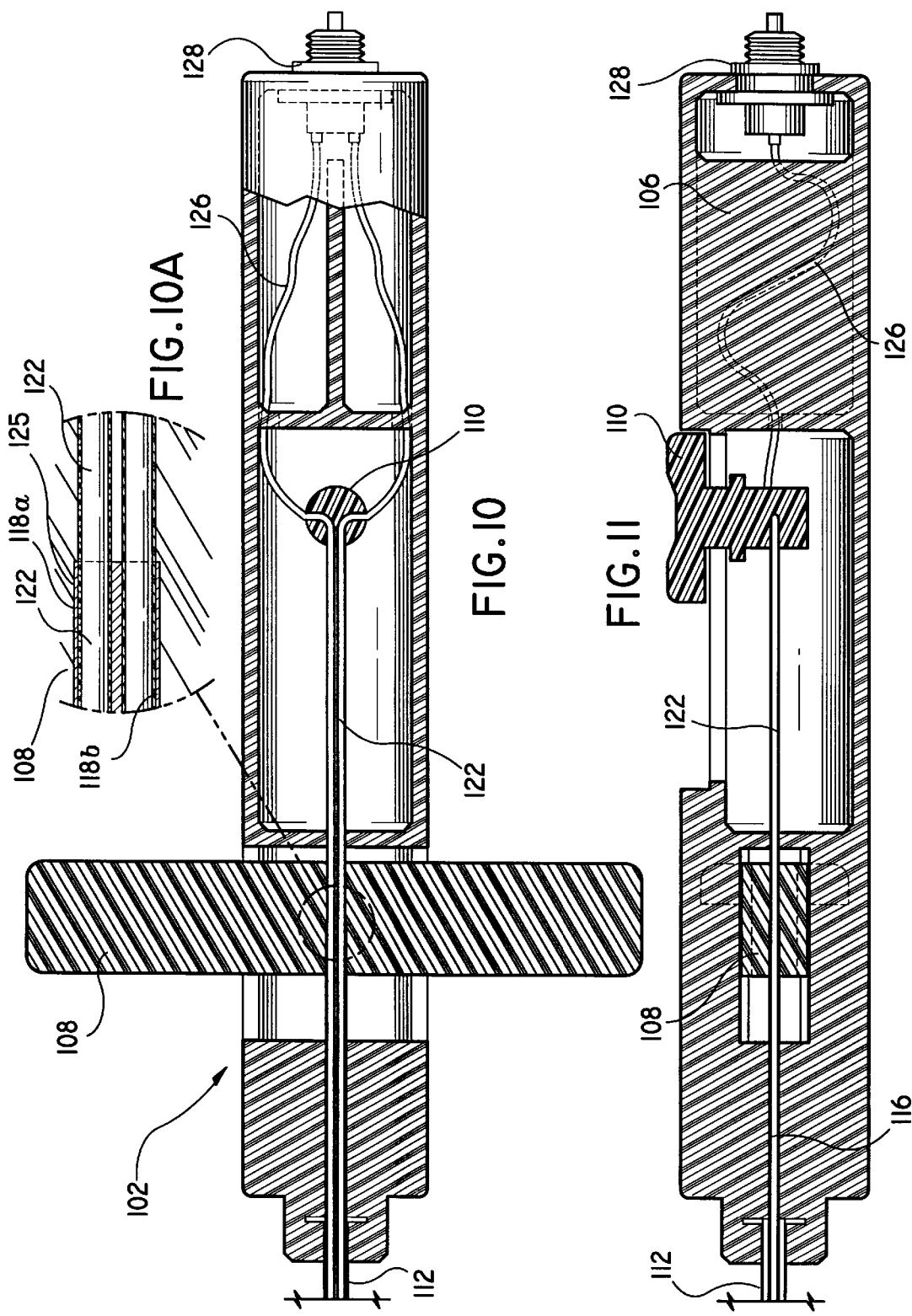

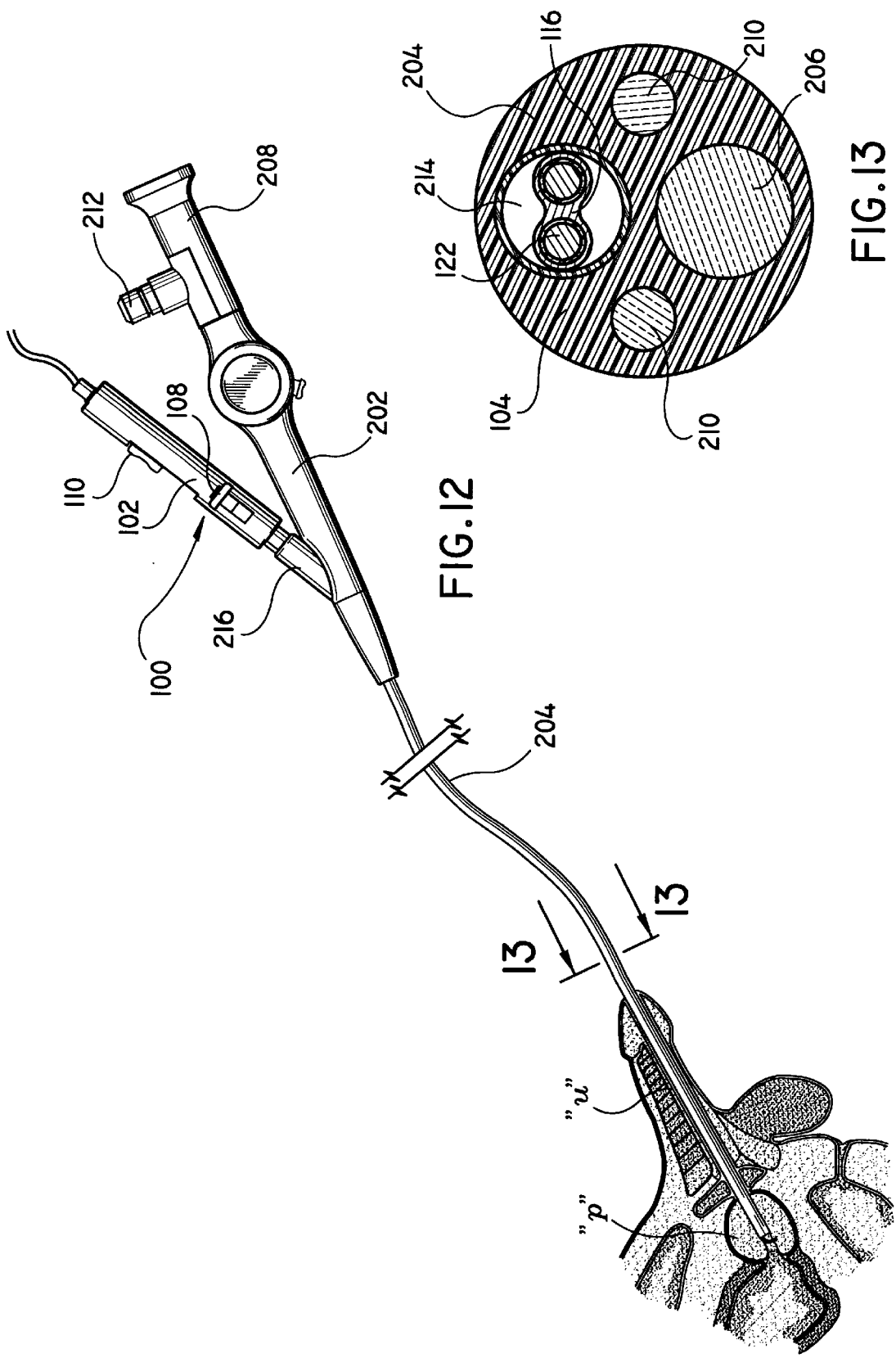

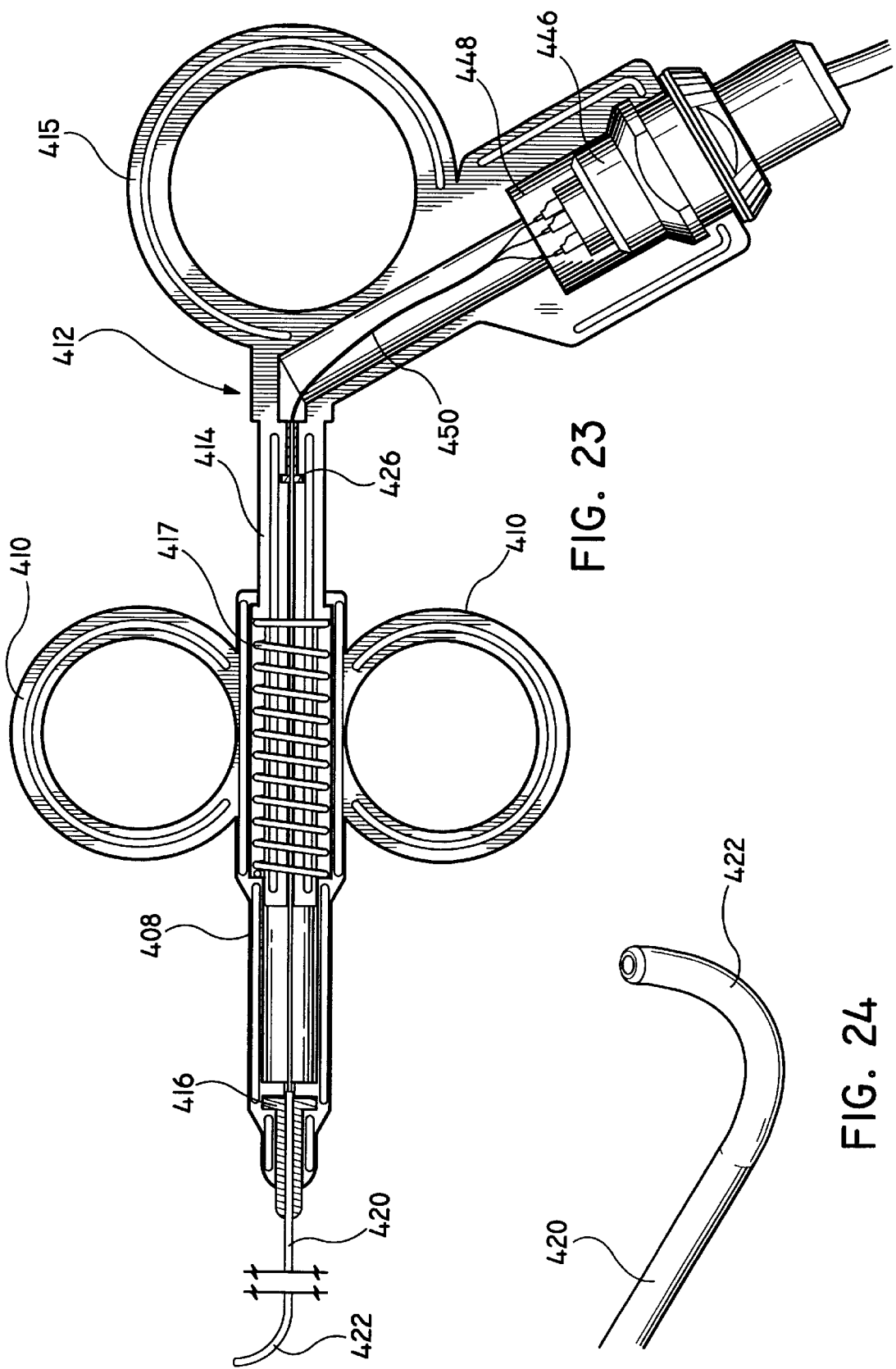

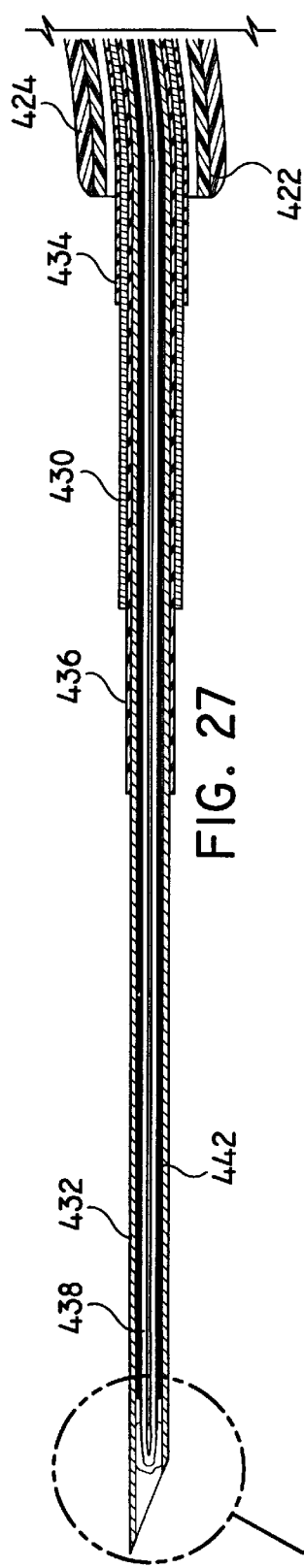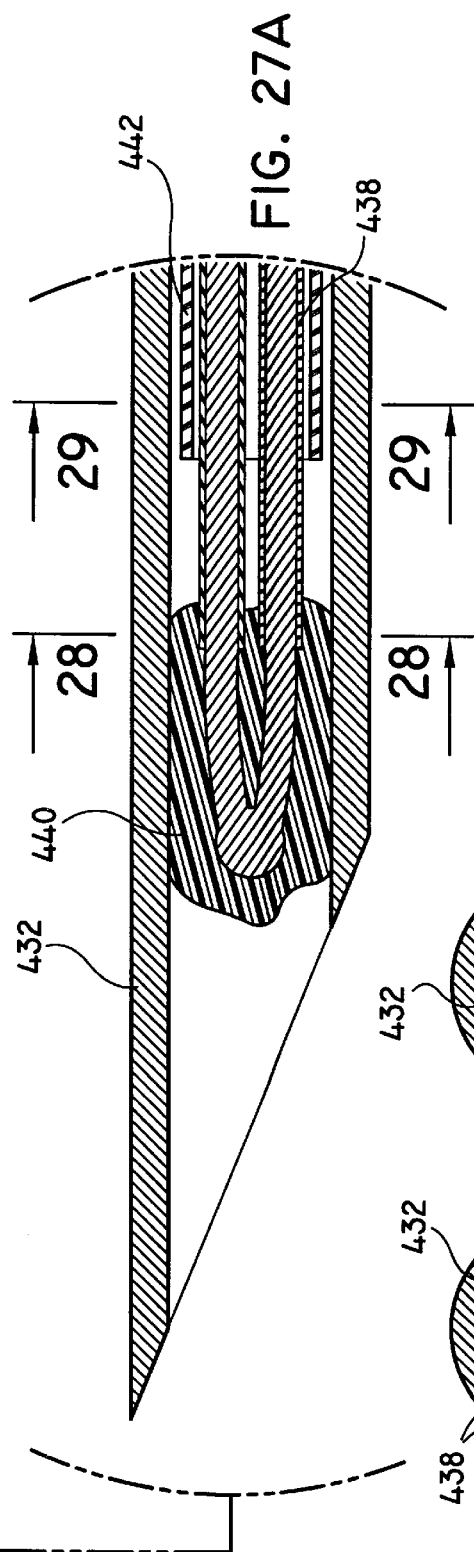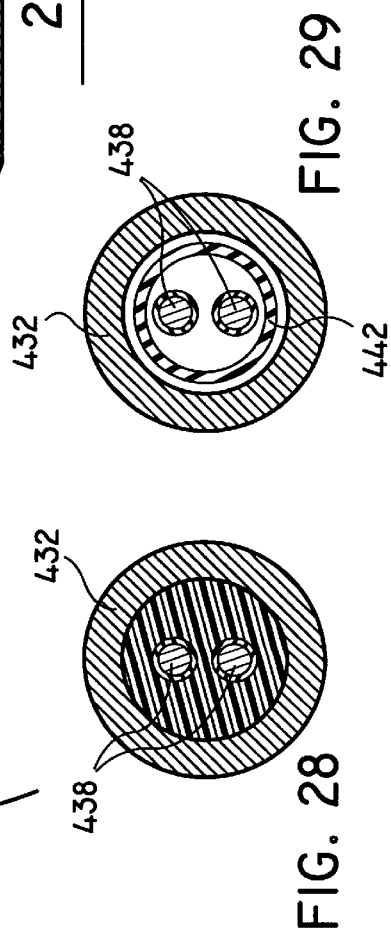

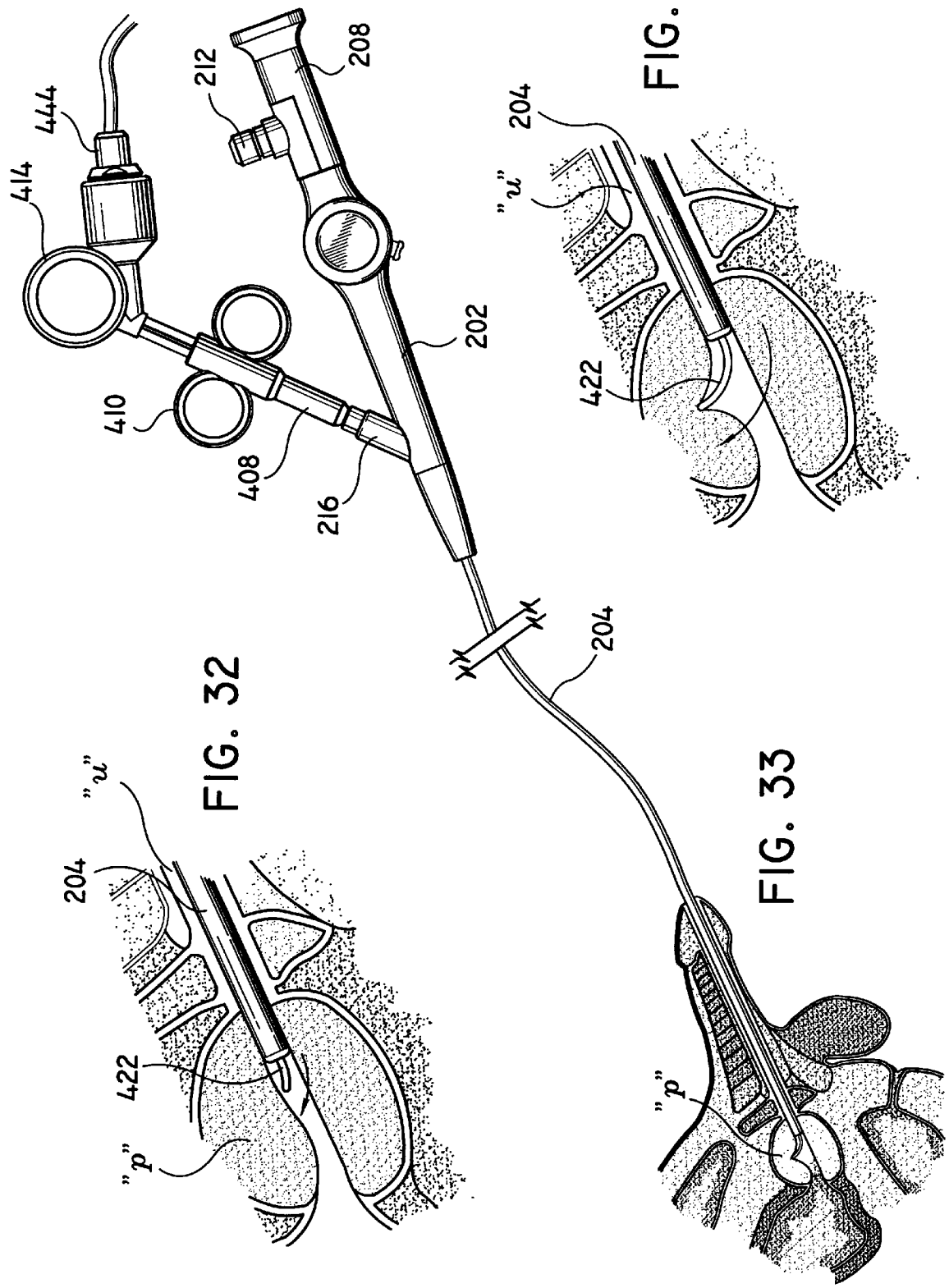

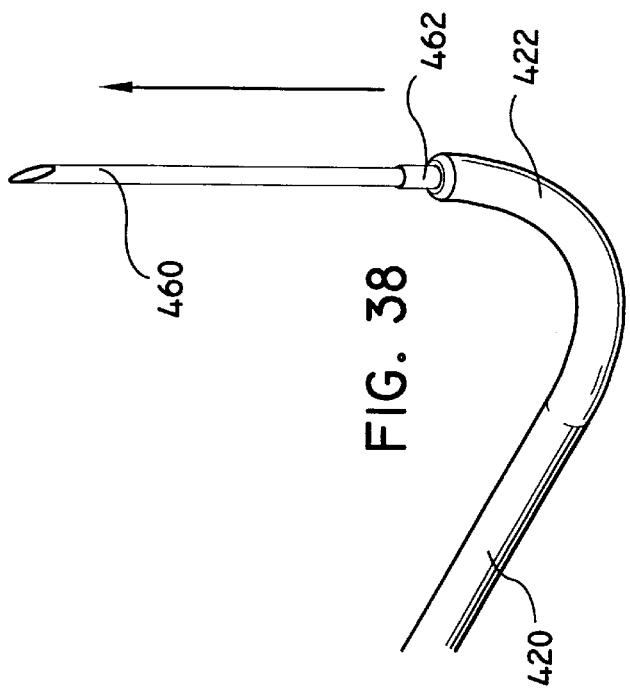
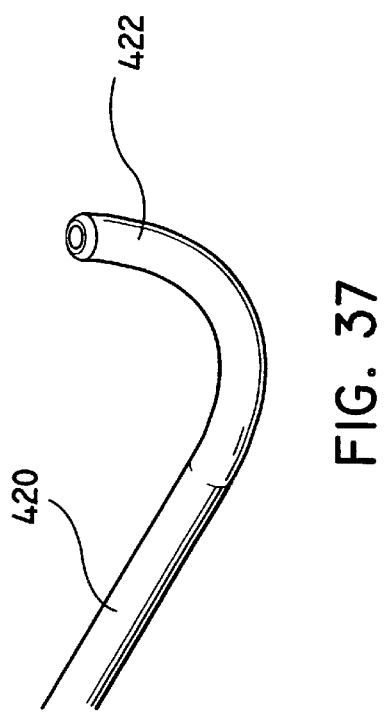
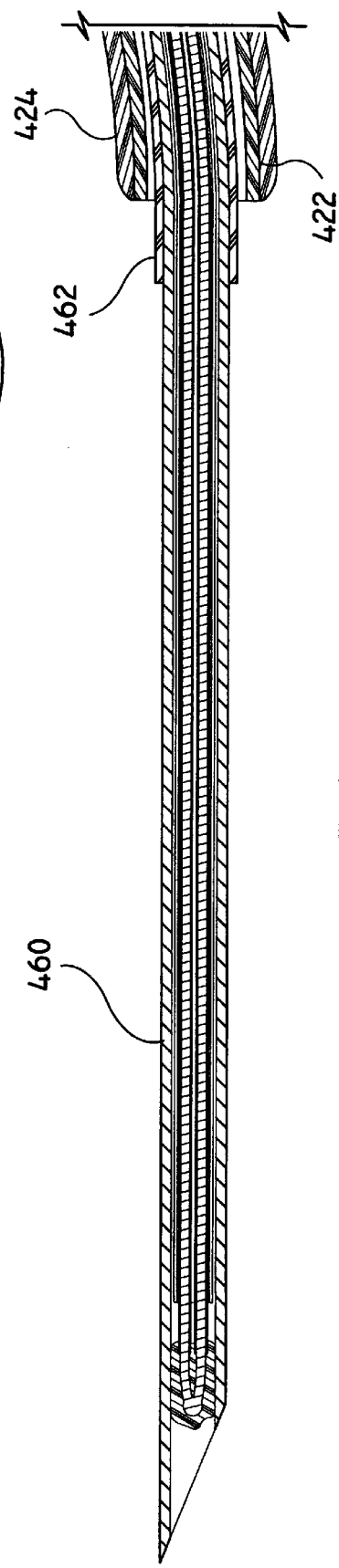
FIG. 37
FIG. 38
FIG. 39

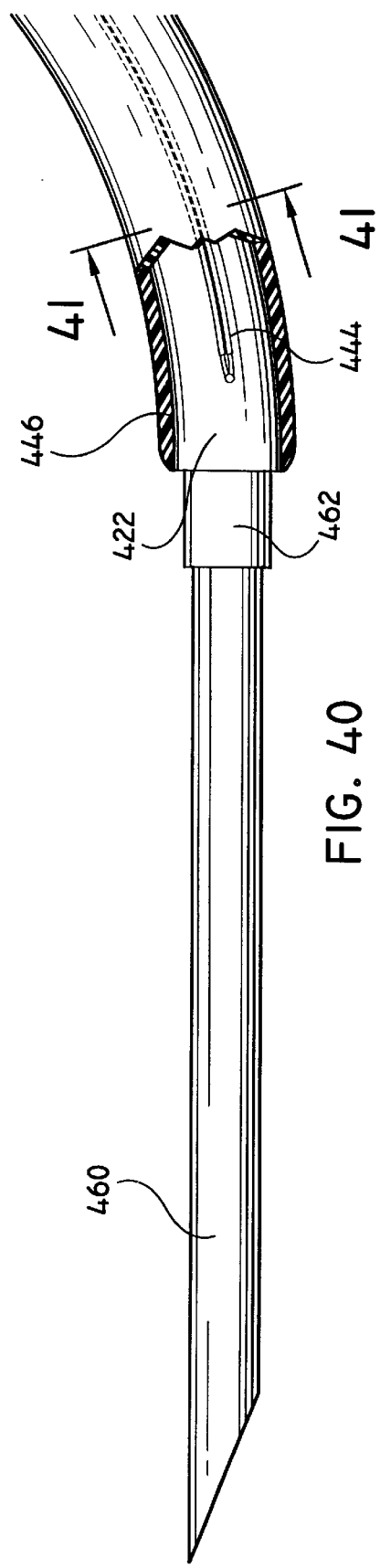
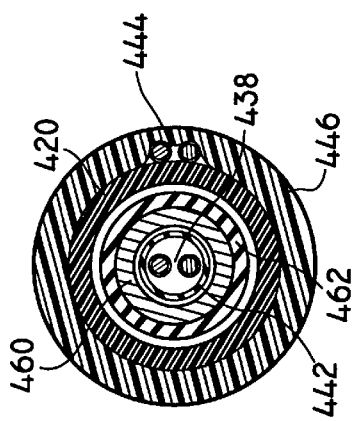
FIG. 40
FIG. 41

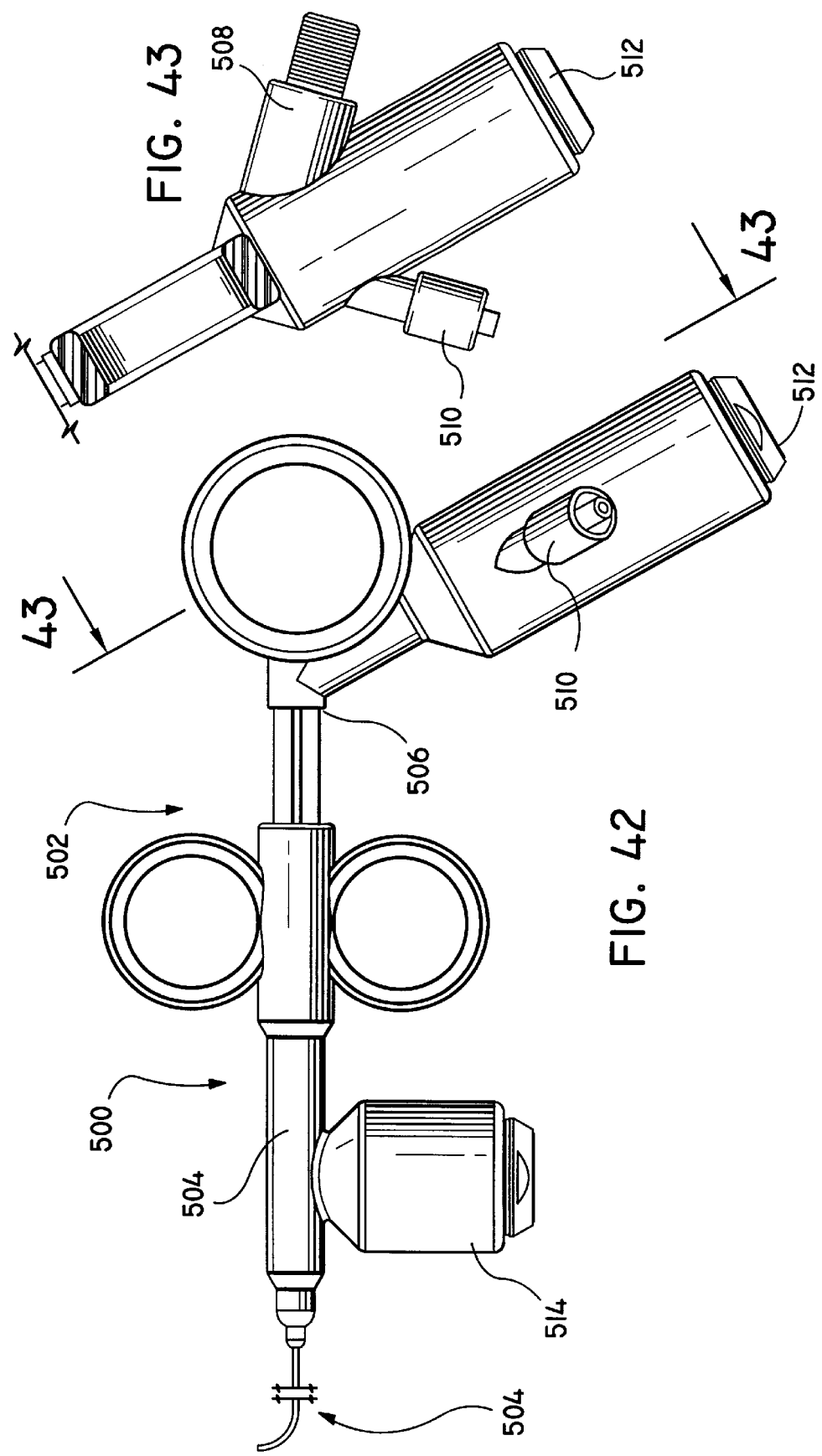

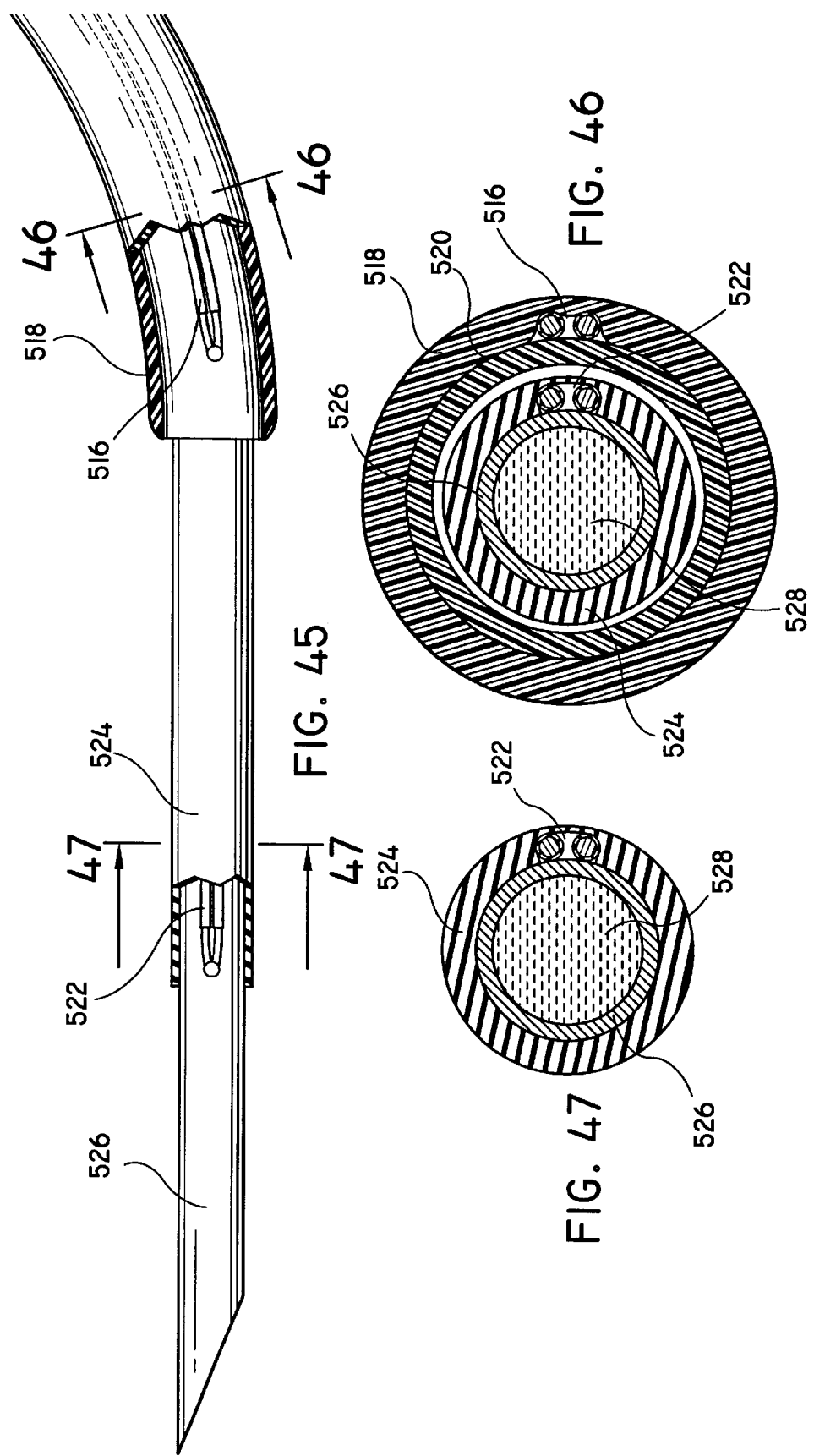

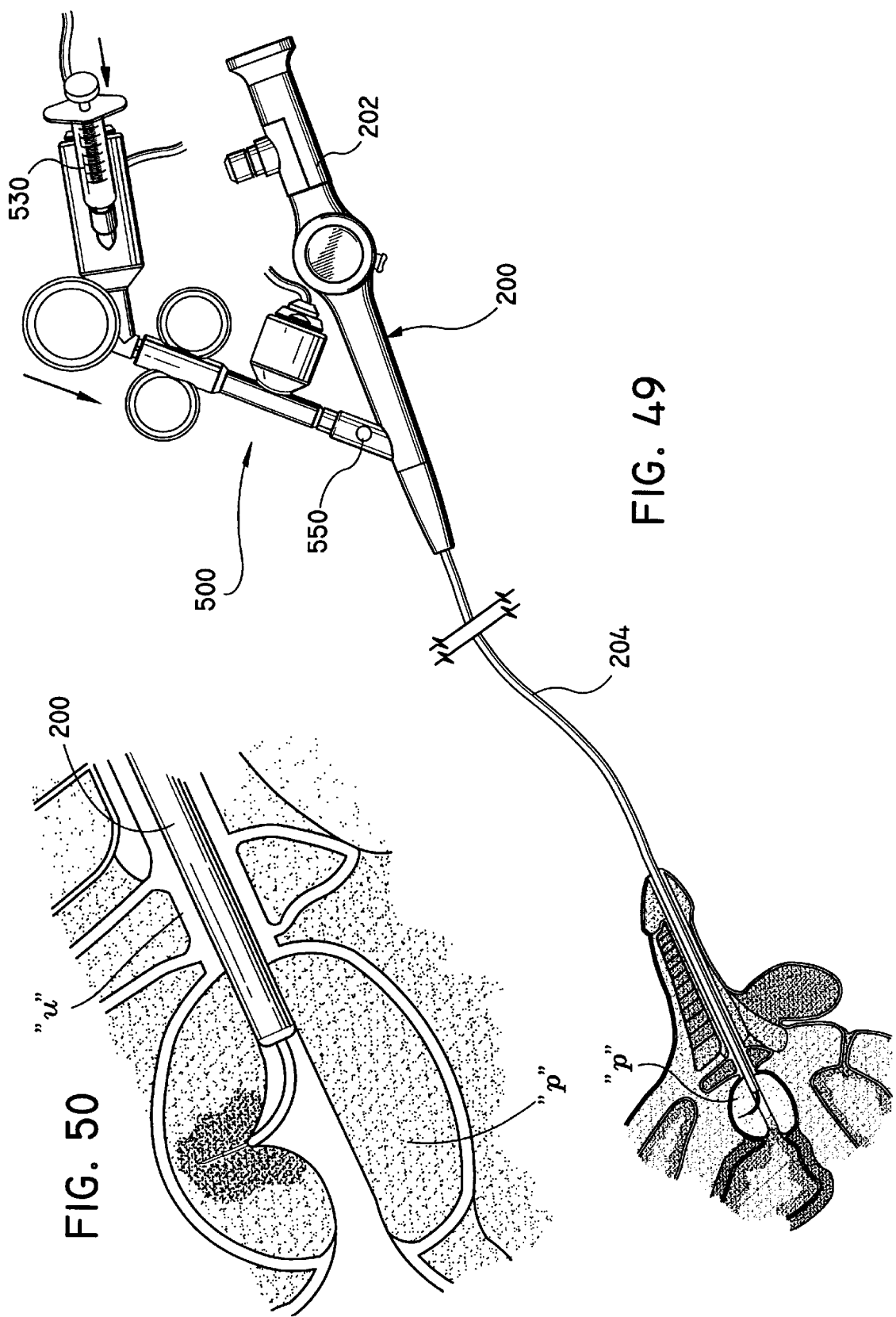

APPARATUS FOR THERMAL TREATMENT OF TISSUE

BACKGROUND

1. Technical Field

The present disclosure relates generally to a method and apparatus for thermal treatment of tissue and, more particularly, to an auxiliary apparatus to be used with a conventional endoscope to provide the endoscope with thermal treatment capabilities. The auxiliary apparatus is particularly contemplated for use with a cystoscope or a urethroscope for hyperthermia treatment of prostatic tissue.

2. Background of the Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, retrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary relief and requiring a subsequent repeat of the procedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

Transurethral microwave therapy (TUMT) and high intensity focused ultrasound (HIFU) have been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applicators of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent form of treatment for BPH involves thermally treating prostatic tissue with radio frequency electromagnetic energy. For example, one current technique, known as transurethral needle ablation (TUNA™), involves the transurethral application of a medical instrument having a built-in RF needle electrode system. The TUNA™ instrument is inserted into the urethra and advanced to a position adjacent the prostate. Thereafter, the RF needles are advanced to penetrate the urethral wall and access the prostatic tissue. The RF system is activated whereby a RF current is transmitted through each electrode to pass through the tissue to a grounding pad thereby forming a necrotic legion which is eventually absorbed by the body. Apparatuses and methods for treating BPH via the TUNA™ technique are disclosed for example in U.S. Pat. No. : 5,366,490.

The TUNA technique has several disadvantages which detract from its usefulness. In particular, the TUNA instruments are generally complex typically incorporating built in optical systems, aspiration systems, etc. . . As a result, the instruments are relatively expensive to manufacture. Moreover, the TUNA instruments are generally enlarged by virtue of the various systems incorporated within the instrument, thus, increasing patient trauma and discomfort during use.

Accordingly, the present disclosure is directed to an auxiliary apparatus for the RF thermal treatment of prostatic tissue. This apparatus is intended for use in conjunction with a conventional endoscope such as a cystoscope and incorporates an RF system and associated mechanism that is at least partially positionable within the working channel of the scope. The apparatus by use in conjunction with a conventional cystoscope makes use of the existing systems, e.g., optical and illumination, of the scope, which effectively results in a less complex and less expensive RF thermal treatment device. Furthermore, the apparatus may be used in cystoscopes as small as 5 mm (or even smaller) in diameter thereby providing a less invasive system for transurethral ablation as compared to the TUNA instruments and technique.

SUMMARY

The present disclosure is directed to an apparatus for thermal treatment of tissue which comprises an elongate portion dimensioned for insertion within a narrow body passage which includes at least one delivery catheter having proximal and distal end portions and a memory portion at the distal end portion thereof. The memory portion is preferably comprised of shape memory material and defines an arcuate configuration when in a normal unstressed condition thereof. An electromagnetic probe is disposed within the one delivery catheter and is longitudinally moveable within the delivery catheter to extend a probe end portion thereof beyond the delivery catheter and within tissue, wherein the electromagnetic probe is adapted to follow the arcuate configuration of the memory portion of the delivery catheter in the normal unstressed condition. The probe is connectable to a thermal energy source.

The present disclosure is also directed to an auxiliary electromagnetic thermal treatment apparatus for use with an endoscope to provide the endoscope with electromagnetic thermal treatment capabilities. The auxiliary apparatus includes a handle portion and an elongate portion connected to the handle portion and dimensioned to be at least partially inserted within a working channel of an endoscope. The elongate portion preferably includes at least one delivery or directional tube having a memory portion comprised of a shape memory material and defining a normally unstressed curved configuration. The one delivery tube is longitudinally moveable relative to the handle portion to extend the memory portion beyond the working channel of the endoscope such that the memory portion assumes the normal unstressed curved configuration thereof. An electromagnetic probe is disposed within the directional tube and is longitudinally moveable relative to the directional tube to extend a probe end portion thereof beyond the directional tube and within tissue. The electromagnetic probe is preferably adapted to follow the curved configuration of the memory portion of the delivery tube for deployment at an angularly oriented relation with respect to the endoscope.

Preferably, a first actuator is mounted to the handle portion and operatively connected to the delivery tube. The first actuator is moveable to move the delivery tube between a first retracted position and a second advanced position. A second actuator is also preferably mounted to the handle portion and is operatively connected to the electromagnetic probe. The second actuator is moveable to extend the probe end portion beyond the delivery tube.

The present disclosure is also directed to a system for thermal treatment comprising an endoscope and an auxiliary thermal treatment device comprising a delivery catheter and an electromagnetic tube insertable within the working channel of the endoscope. A method for thermally treating tissue is also disclosed utilizing an endoscope and a thermal treatment apparatus.

BRIEF DESCRIPTION OF THE DRAWINGS

Preferred embodiment(s) of the present disclosure are described herein with reference to the drawings wherein:

FIG. 1 is a perspective view of the auxiliary apparatus for thermal treatment of tissue in accordance with the principles of the present disclosure;

FIG. 2 is a cross-sectional view taken along the lines 2—2 of FIG. 1 illustrating the outer sleeve, the probe delivery unit disposed within the outer sleeve and the electrodes disposed within the delivery tubes of the delivery unit;

FIG. 3 is a side elevational view of the probe delivery unit;

FIG. 4 is an axial view of the probe delivery unit as viewed from its proximal end;

FIG. 5 is an axial view of the probe delivery unit as viewed from its distal end;

FIG. 6 is a top elevational view of the probe delivery unit;

FIG. 6A is a perspective view of the distal end of the probe delivery unit;

FIG. 7 is a side elevational of the handle of the apparatus of FIG. 1;

FIG. 8 is a cross-sectional view taken along the lines 8—8 of FIG. 7;

FIG. 9 is a cross-sectional view taken along the lines 9—9 of FIG. 7;

FIG. 10 is a top cross-sectional view of the handle illustrating the first and second actuators of the handle;

FIG. 10A is an isolated view illustrating connection of the probe delivery unit to the first actuator;

FIG. 11 is a side cross-sectional view of the handle further illustrating the connection of the second actuating member to the electrodes;

FIG. 12 is a view illustrating insertion of a cystoscope with mounted auxiliary thermal treatment apparatus within the urethral passage of the patient;

FIG. 13 is a cross-sectional view taken along the lines 13—13 of FIG. 12 illustrating the apparatus of FIG. 1 positioned within the working channel of the cystoscope;

FIG. 23 is a side plan view of the apparatus with the handle in cross-section;

FIG. 24 is a perspective view of the distal end of the elongate portion of the apparatus;

FIG. 27 is an enlarged cross-sectional view of the distal end of the electrode assembly and deployed beyond the directional tube;

FIG. 27A is an enlarged isolated view of the distal tip of the electrode assembly with a thermocouple positioned therein for detecting the temperature at the treatment area;

FIG. 28 is a cross-sectional view taken along the lines 28—28 of FIG. 27A;

FIG. 29 is a cross-sectional view taken along the lines 29—29 of FIG. 27A;

FIG. 32 is a view illustrating insertion of a cystoscope and mounted thermal treatment apparatus within the urethral passage with the directional tube partially deployed;

FIG. 33 is a view illustrating the cystoscope and mounted apparatus inserted within the urethral passage with the directional tube fully deployed;

FIG. 34 is an enlarged view further illustrating the directional tube deployed;

FIG. 37 is a view of an alternate embodiment of the auxiliary thermal treatment apparatus of FIG. 21 incorporating a monopolar electrode assembly;

FIG. 38 is a perspective view of the distal end of the electrode assembly with the monopolar electrode deployed beyond the distal end of the directional tube;

FIG. 39 is a cross-sectional view of the electrode illustrating a thermocouple disposed within the electrode for detecting the temperature of the treatment area;

FIG. 40 is a side plan view of the electrode and directional tube with the directional tube partially cut-away to illustrate a second thermocouple for detecting the temperature of the tissue adjacent the treatment area;

FIG. 41 is a cross-sectional view taken along the lines 41—41 of FIG. 40;

FIG. 42 is a side plan view of another alternate embodiment of the auxiliary thermal treatment apparatus incorporating a dissipating agent for facilitating transfer of the electromagnetic energy to the treated tissue;

FIG. 43 is a view taken along the lines 43—43 of FIG. 42 depicting components of the handle of the apparatus of FIG. 42;

FIG. 45 is a side plan view of the distal end of the elongate portion with portions of the directional tube and the electrode assembly cut-away;

FIG. 46 is a cross-sectional view taken along the lines 46—46 of FIG. 45;

FIG. 47 is a cross-sectional view taken along the lines 47—47 of FIG. 45;

FIG. 49 is a view illustrating the cystoscope and mounted thermal treatment apparatus inserted within the urethral passage; and FIG. 50 is an isolated view illustrating deployment of the electrode assembly within the prostatic tissue.

DETAILED DESCRIPTION OF PREFERRED EMBODIMENTS

Figure 16:
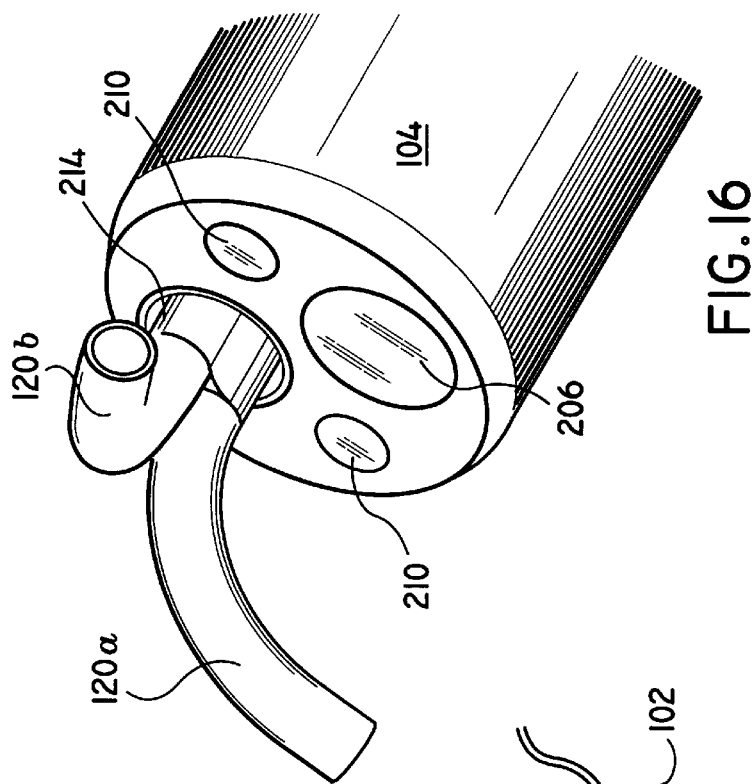
FIG. 16 is a view similar to the view of FIG. 14 illustrating deployment of the distal end of the delivery tubes of the probe delivery unit whereby the distal end assumes its normal unstressed condition angularly oriented relative to the longitudinal axis of the apparatus.

The apparatus of the present disclosure is intended to deliver electromagnetic energy to tissue for thermal treatment of the tissue including tissue ablation, tissue vaporization and/or tissue coagulation. The apparatus has particular application in the treatment of benign prostate hyperplasia (BPH) with electromagnetic radio frequency (RF) energy, however, it is to be appreciated that the apparatus is not limited to such application. For example, the apparatus is not limited to the treatment of BPH, but, may be used in other surgical procedures such as cardiac ablation, cancer treatment, etc. . . Moreover, the apparatus may be used in any minimally invasive procedure where thermal treatment of tissue is desired and access to the tissue is limited.

The apparatus is particularly intended to be used in conjunction with an endoscope such as a cystoscope, fiber scope, laparoscope, urethroscope, etc . . . to provide the scope with thermal treatment capabilities. More specifically, the apparatus is at least partially insertable within the working channel of an endoscope, which is positioned in the body to access a targeted tissue area, to thermally treat the desired tissue.

Referring now to FIGS. 1–2, apparatus 100 includes handle 102 and elongate body 104 connected to the handle 102 and extending distally therefrom. Handle 102 includes frame 106 which is preferably fabricated from a suitable rigid polymeric material or, in the alternative, from stainless steel or an aluminum alloy. Frame 106 is advantageously dimensioned to be grasped by the hands of the surgeon. Handle 102 further includes first and second actuators 108, 110 which are mounted for movement relative to the frame 106 to operate the apparatus.

Elongate body 104 may include outer sleeve 112 preferably fabricated from a flexible material such as Nitinol. It is envisioned that outer sleeve 112 may alternately be rigid if, for example, it is intended to be used with a rigid scope. Outer sleeve 112, if provided, ranges from about 25 to about 40 millimeters (mm) in length, preferably, about 37 mm and ranges from about 1.5 to about 2.5 millimeters in diameter, preferably about 2.3 mm. Outer sleeve 112 defines axial bore 114 extending therethrough. Other dimensions are also contemplated. Alternatively, the outer sleeve may be eliminated.

Referring now to FIGS. 2–6A, in conjunction with FIG. 1, probe delivery unit, identified generally by reference numeral 116, is disposed within axial opening 114 of outer sleeve 112. Probe guide 116 is adapted for reciprocal longitudinal movement within the opening 114 and includes first and second hollow delivery (directional) tubes 118a, 118b. Delivery tubes 118a, 118b are preferably connected to each other for a major portion of their respective lengths, but are separated at the distal end portions 120a, 120b as best depicted in FIGS. 6 and 6A. Delivery tubes 118a, 118b accommodate electromagnetic probes 122 therein (FIG. 2) and function in guiding the probes 122 at desired orientations within the tissue.

Referring particularly to FIGS. 3–6A, delivery tubes (or catheter) 118a, 118b of probe guide 116 are preferably fabricated from a shape memory metal such as NITINOL and are preferably joined to each other by welding or with the use of adhesives. In the normal condition of delivery tubes 118a, 118b, the distal ends 120a, 120b of the tubes 118a, 118b each assume the arcuate configuration depicted in FIGS. 3–6A, i.e., the distal end portions 120a, 120b have memory to define the arcuate orientation as shown, thus, providing arcuate paths for electromagnetic probes 122 to follow to penetrate the tissue. The particular orientation of memory portions 120a, 120b of delivery tubes 118a, 118b can be varied depending on the objectives of the surgical procedure. The distal end or memory portions 120a, 120b of delivery tubes 118a, 118b readily adapt a linear configuration when confined in the outer sleeve 112 of elongated portion 104 as will be discussed.

In a preferred embodiment (e.g., in BPH application), memory portions 120a, 120b of delivery tubes 118a, 118b define a radius of curvature "r" ranging between about 0.250 to about 0.400 inches, preferably about 0.312 inches. Memory portions 120a, 120b are also separated by an angle "T" ranging from about 45° to about 90° (degrees). Clearly other dimensions and angular orientations of memory portions 120a, 120b are contemplated as well.

With reference again to FIG. 2, electromagnetic probes 122 disposed within delivery tubes 118a, 118b include bipolar electrodes formed of a thin solid wire capable of carrying an electromagnetic radiofrequency (RF) current. The electrodes are relatively flexible to follow along the path defined by delivery tubes 118a, 118b, but, sufficient in rigidity to be advanced into tissue. The electrodes are preferably made of Nitinol so they can return to their normally straight configuration after being bent by the delivery tubes. The electrodes each have a pointed tip to facilitate penetration through the tissue. Each electrode has an insulating layer, designated by reference numeral 124, which extends along a major portion of its length to prevent damage to non-targeted body tissue. Each electrode is therefore electrically isolated from its delivery tube. Insulating layer 124 terminates to expose the distal penetrating portions of the electrodes 122, thus, permitting the transmission of electromagnetic RF current to the targeted body tissue. Alternatively, monopolar electrodes could be provided.

Referring now to FIGS. 7–11, probe unit 116 extending through outer sleeve 112 is operatively connected to first actuator 108. In a preferred arrangement, first actuator 108 includes an inner recess 125 which receives the proximal end of probe guide 116 in interfitting relation as depicted in FIG. 10A. Other mounting arrangements for connecting actuator 108 and probe guide 116 are envisioned as well such as the use of adhesives, screws, or the like. Longitudinal movement of first actuator 108 causes corresponding longitudinal movement of probe delivery unit 116 within outer sleeve 112. That is, first actuator 108 is moveable to cause reciprocal movement of probe guide 116 between a first retracted position where the distal end or memory portions 120a, 120b of guide 118a, 118b are contained within outer sleeve 112 and a second advanced position where the memory portions 120a, 120b extend beyond the distal end of outer sleeve 112 and assume their angularly oriented positions as will be discussed hereinbelow.

Second actuator 110 is operatively connected to electromagnetic probes 122 disposed within delivery tubes 118a, 118b. Any conventional means appreciated by one skilled in the art for connecting actuator 110 to electromagnetic probes 122 may be utilized. In the preferred embodiment, an interfitting relationship of the proximal ends of electromagnetic probes 122 with an inner recess of second actuator 110 (such as the arrangement disclosed above with first actuator 108) will be employed. Second actuator 110 is moveable to cause corresponding motion of electromagnetic probes 122 within their respective delivery tubes 118a, 118b to extend the penetrating end portions of the probes 122 beyond the tubes for deployment into tissue.

As seen in FIGS. 7, 10 and 11, a pair of conductive wires 126 are provided to connect electromagnetic probes 122 to coupling 128 mounted to handle 104. Coupling 128 is connectable to an external radio frequency energy source "s" as schematically depicted in FIG. 1.

Referring now to FIG. 12, apparatus 100 is shown positioned within a conventional cystoscope 200 for thermal treatment of prostrate "p" to alleviate the symptoms of BPH. One conventional cystoscope 200 with which the apparatus of the present disclosure can be utilized is the ACN Flexible CystoNephroscope manufactured by Circon ACMI. Cystoscope 200 includes handle 202 and a flexible elongated portion 204 connected to the handle 202 and extending distally therefrom. Cystoscope 200 incorporates an optical system to permit viewing of the tissue to be treated. As depicted in FIG. 13, the optical system preferably consists of flexible fiber optic bundles (identified by reference numeral 206) which are accommodated within a longitudinal bore extending through the elongated portion 204 of the scope 200. The fiber optic bundles 206 extend to eyepiece 208 where the surgeon can view the image transmitted by the optical system.

Cystoscope 200 also includes an illumination system which provides illuminating light to the targeted tissue area. The illumination system includes a plurality of optical fibers 210 which are accommodated within a plurality of longitudinal channels (two are shown) of elongated portion 204 and extend within handle 202 where they terminate at illumination coupler 212. Illumination coupler 212 is connectable to a conventional light source as is known in the art. Cystoscope 200 further includes a working channel 214 extending through flexible elongated portion 204 and terminating at channel port 216 of handle 202. Working channel 214 is adapted to receive various surgical instrumentation through channel port 216 (e.g., thermal treatment apparatus 100) to permit the performance of surgical procedures at the distal end of the cystoscope 200. Cystoscope 200 is preferably a 5 mm scope.

Operation

The use of apparatus 100 with cystoscope 200 in conjunction with the thermal treatment of prostatic tissue will now be discussed. Cystoscope 200 is inserted through urethral passage "u" of the patient and advanced within the passage until the distal end of the scope is adjacent prostate gland "p". Thereafter, elongate body 104 of apparatus 100 is inserted into working channel 214 of cystoscope 200 and advanced into the working channel 214 until handle 102 of the apparatus contacts channel port 216 of scope handle 202. As an alternative method of insertion, apparatus 100 may be positioned within cystoscope 200 prior to insertion within the urethral passage "u" and the entire assembly may be then advanced within the urethral passage. It is envisioned that handle 102 of apparatus 100 may incorporate a locking mechanism to lockingly engage channel port 216 of handle 202 of the cystoscope 200.

Figure 15:
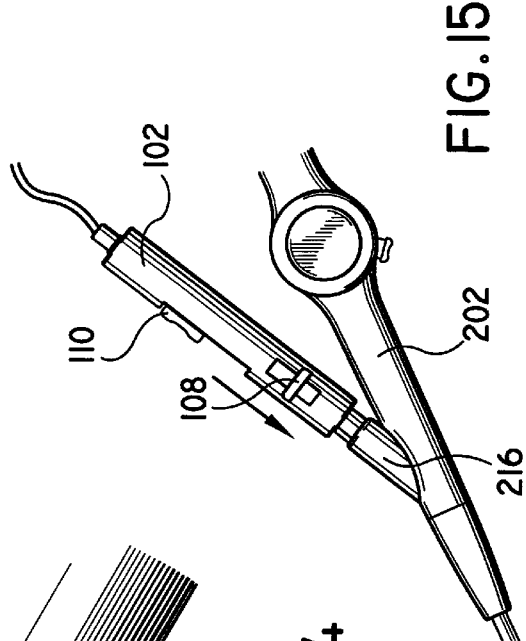
FIG. 15 is a view illustrating distal movement of the first actuator to deploy the distal end portion of the delivery tubes of the probe delivery unit.
Figure 14:
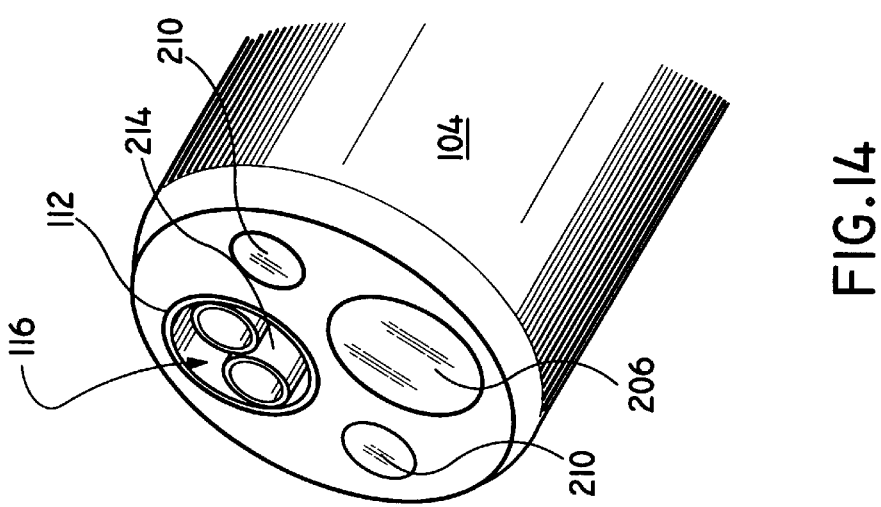
FIG. 14 is an enlarged perspective view of the distal end portion of the cystoscope illustrating the delivery tubes of the probe delivery unit contained within the working channel of the scope.

With reference now to FIG. 14, probe delivery unit 116 is shown in its retracted position. In such position, the distal end portions 120a, 120b of delivery tubes 118a, 118b are constrained by outer sleeve 112 (and elongated portion 204 of scope 200) thereby assuming a general linear configuration within the sleeve 112. Thereafter, first actuator 108 is distally advanced as depicted in FIG. 15 to move probe delivery unit 116 from its retracted position of FIG. 14 to its extended position of FIG. 16. Upon exiting working channel 214 of cystoscope 200, the distal ends or memory portions 120a, 120b of delivery tubes 118a, 118b are no longer constrained by outer sleeve 112, and, thus are free to assume their normal unstressed curved configurations depicted in FIG. 16 and FIG. 16A. By exiting through the distal end face of the working channel 214 of cystoscope 200, the deployment of delivery tubes 118a, 118b can be monitored with the optical system of cystoscope 200. That is, both 0 degree and oblique viewing is achieved. In the extended position of delivery tubes 118a, 118b, the distal end portions 120a, 120b may slightly extend beyond the outer circumference of scope 200, but, however, do not penetrate the urethral lining. It is to be noted that the degree of deployment of memory portions 120a, 120b of delivery tubes 118a, 118b may be selected to thereby achieve desired angular orientations of the memory portions 120a, 120b, consequently, controlling the orientation of the deployed electrodes. (As noted above, alternately, outer sleeve 112 need not be provided and the apparatus is advanced through the working channel to expose the delivery tubes.)

Figure 17:
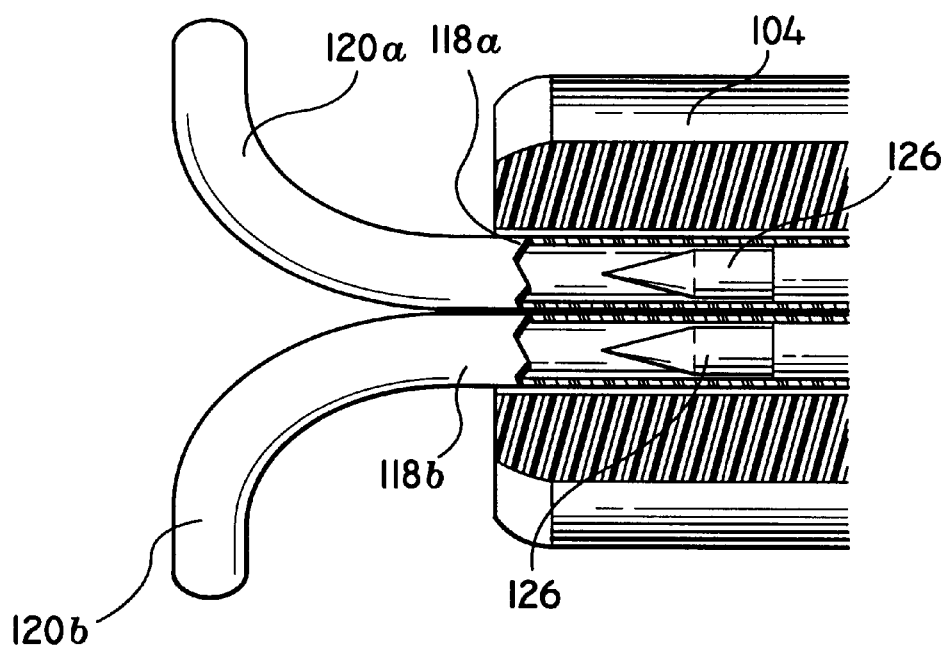
FIG. 17 is a side plan view of the distal end of the cystoscope in partial cross-section further illustrating deployment of the delivery tubes with the electrodes in a retracted position disposed within the tubes.
Figure 18:
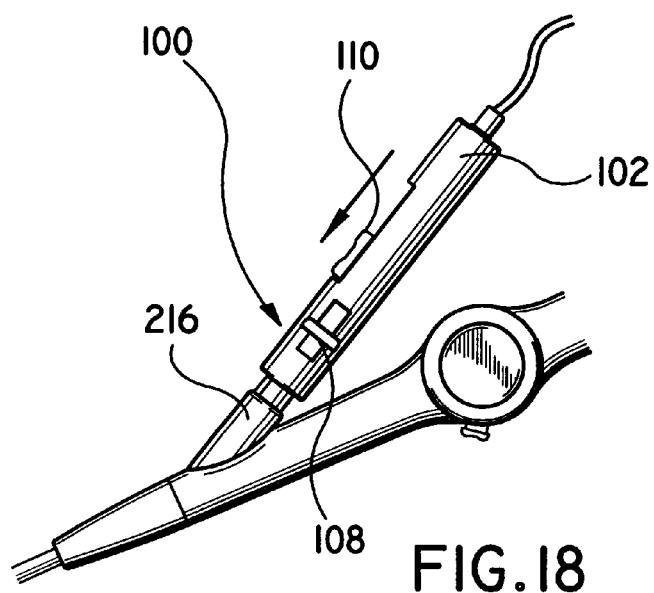
FIG. 18 is a view similar to the view of FIG. 15 illustrating distal movement of the second actuating member to advance the electrodes through the delivery tubes of the probe delivery unit and within the patient's prostatic tissue.
Figure 19:
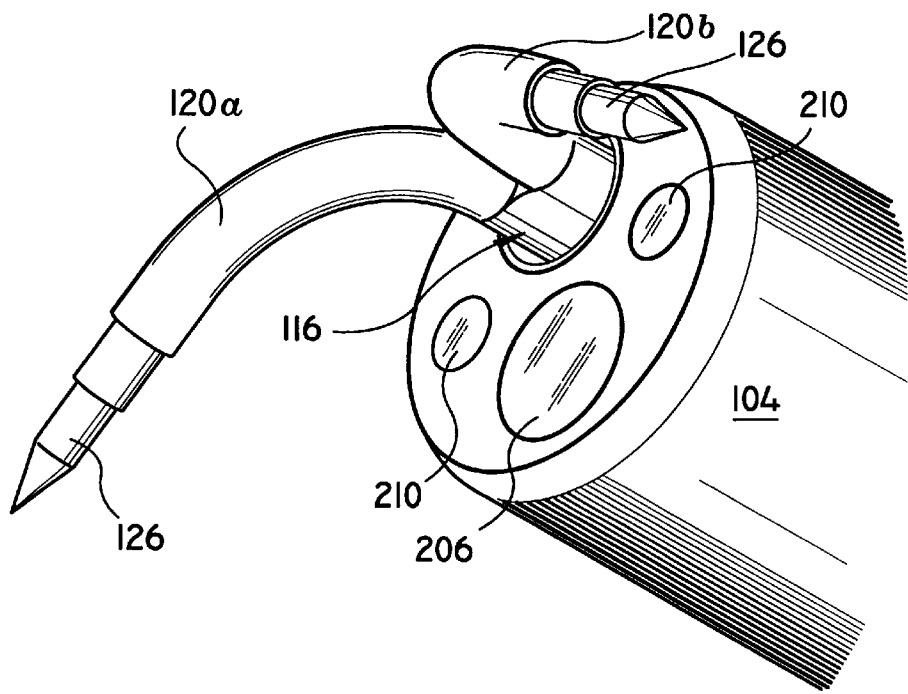
FIG. 19 is a view similar to the view of FIG. 16 illustrating the electrodes in the advanced position.

Referring now to FIGS. 17–19, with distal end portions 120a, 120b in their extended positions, attention is directed to deploying the electromagnetic probes 122. FIG. 17 depicts the electromagnetic probes 122 in their retracted position within delivery tubes 118a, 118b. Second actuator 110 is selectively distally advanced to advance electromagnetic probes 122 from delivery tubes 118a, 118b as depicted in FIG. 18. During advancing movement, the penetrating end portions 126 of probes 122 flex or bend to conform to the curved configuration of memory portions 122a, 122b of the delivery tubes 118a, 118b to pierce the urethral wall "u" and enter the prosthetic tissue "p". The degree of deployment of electromagnetic probes 122 may be selectively controlled (e.g., partial deployment) with second actuator 110 to thereby provide a level of control over the thermal treatment field generated by the probe.

The system is then energized to thermally treat (e.g., ablate, vaporize or cauterize) the desired prosthetic tissue with RF energy. As a result of this treatment, the prosthetic tissue BPH necroses and dies, thus, relieving pressure off the urethral wall and alleviating the symptoms of BPH. During treatment, the depth of penetration of penetrating end portions 126 of electromagnetic probes 122 may be selectively adjusted by movement of second actuator 110 to permit specific regions of the prosthetic tissue "p" to be targeted for thermal treatment thus providing heating pattern flexibility and control. During treatment, insulating layer 124 of electromagnetic probes 122 preferably contact the urethral wall "u" to prevent damage to the wall.

Upon completion of the procedure, the system is de-energized and the cystoscope 200 and apparatus are removed from the urethral passage "u".

Figure 20:
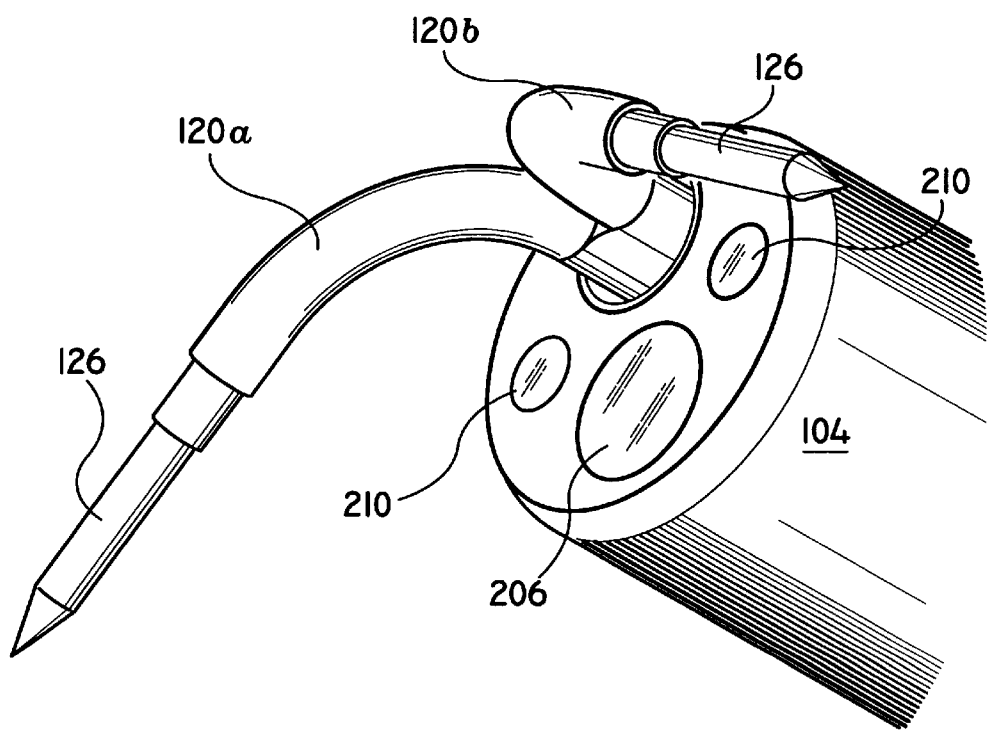
FIG. 20 is a view of an alternate embodiment of the auxiliary thermal treatment apparatus where a greater portion of the electrode is exposed to provide an increased thermal treatment capacity.

FIG. 20 is a perspective view of the distal end of cystoscope 200 with an alternate auxiliary thermal treatment apparatus mounted within the working channel 214 (FIG. 13) of the scope. This thermal treatment apparatus is identical to the apparatus described in connection with FIG. 1 except that in accordance with this embodiment, a greater portion or length of the inner electromagnetic probe 122 is exposed (i.e., uninsulated) to increase the thermal treatment region generated by the probes (Compare with FIG. 19). It is to be appreciated that the lengths of the exposed electrode portions i.e. the length of insulation, may be varied to achieve desired thermal treatment objectives.

Figure 21:
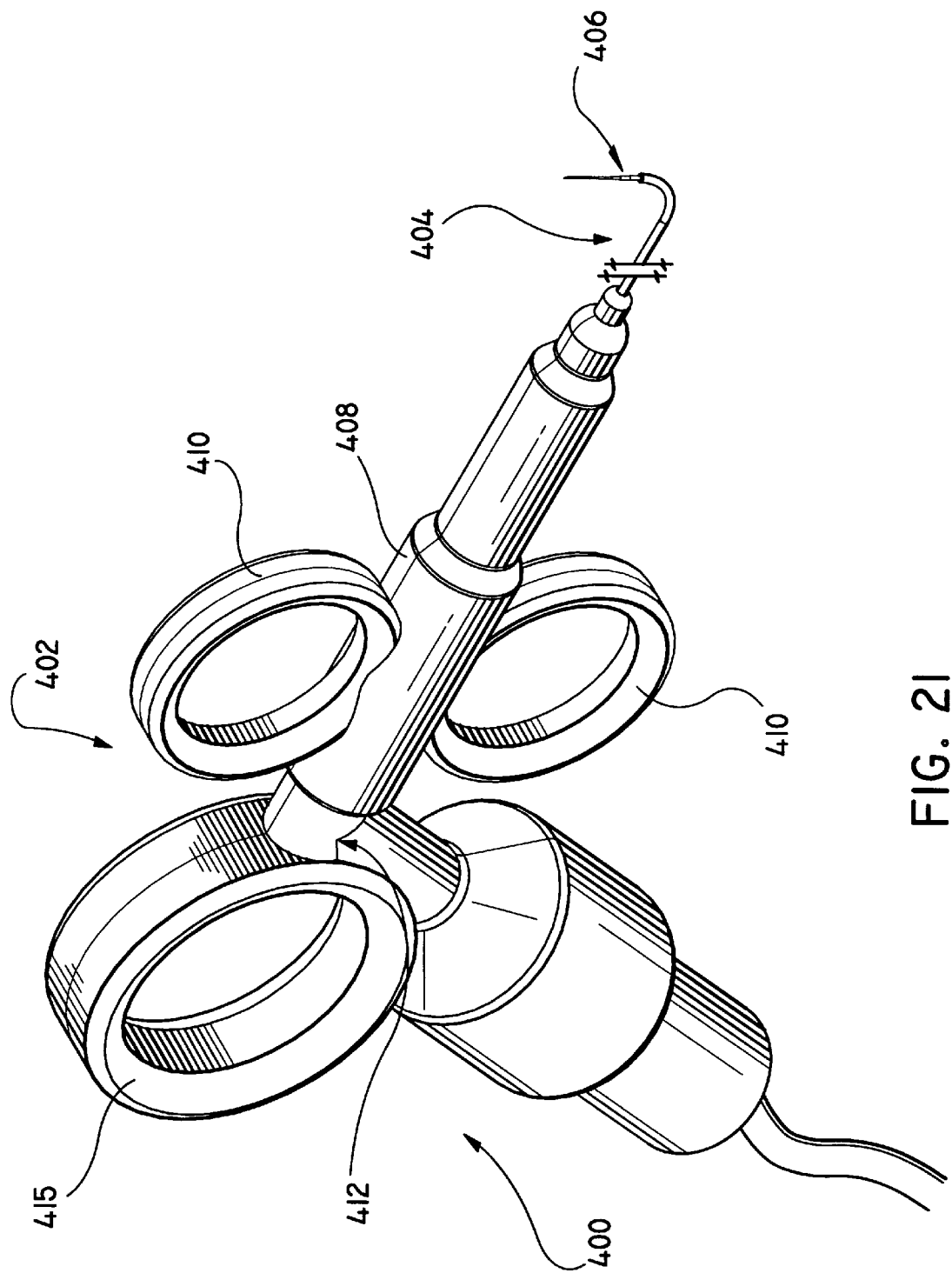
FIG. 21 is a perspective view of another alternate embodiment of the auxiliary apparatus for thermal treatment of tissue incorporating a coaxial arranged bipolar electrode assembly.
Figure 22:
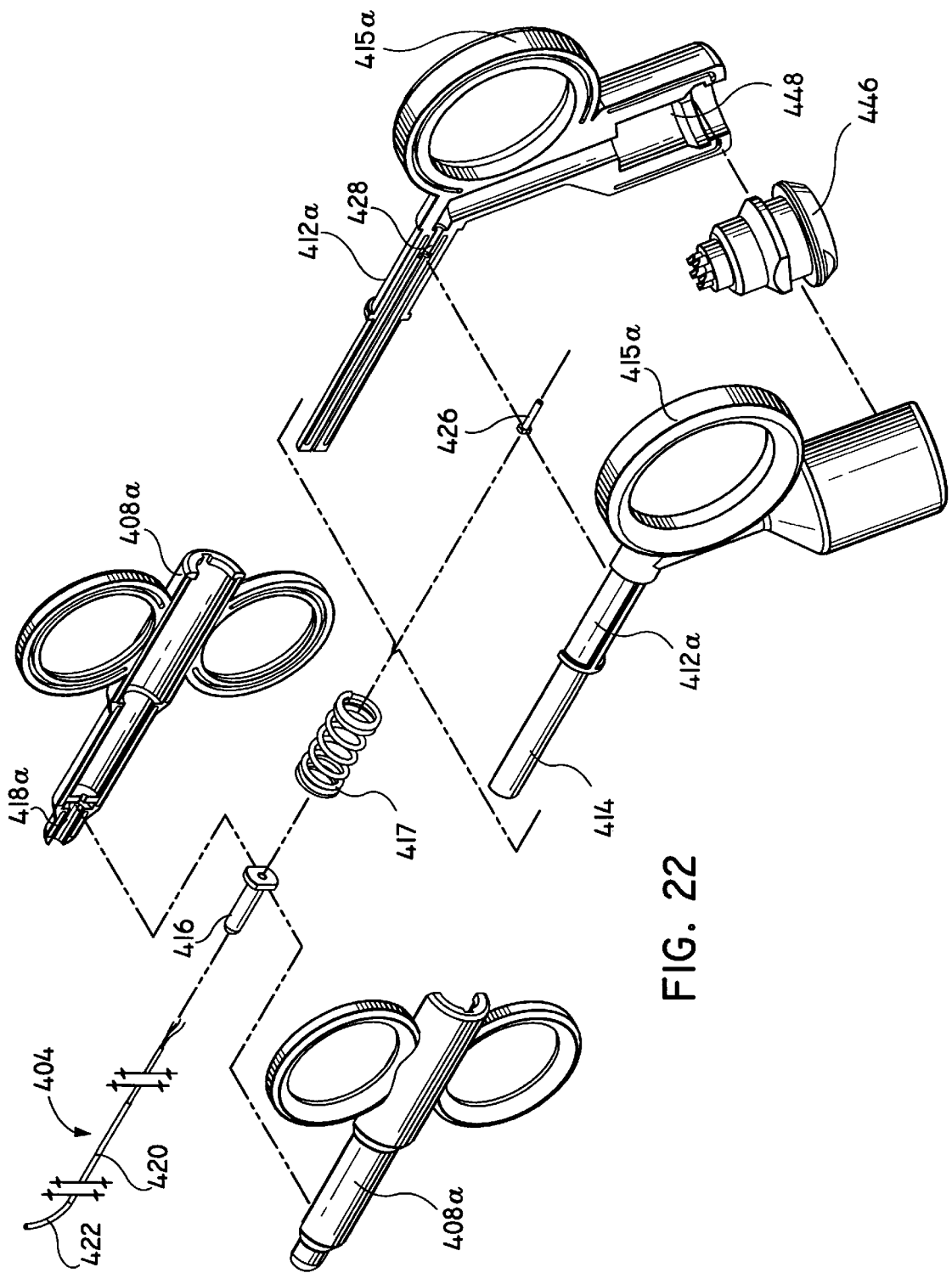
FIG. 22 is a perspective view with parts separated of the auxiliary apparatus of FIG. 21.

Referring now to FIGS. 21–23, there is illustrated another alternate embodiment of the auxiliary RF thermal treatment apparatus of the present disclosure. Apparatus 400 includes housing or handle 402, elongate portion 404 connected to the handle and extending distally therefrom, and a bipolar or monopolar electrode unit 406 which extends beyond the distal end of the elongate portion 404. Handle 402 includes frame 408 defining a generally cylindrical configuration and having diametrically opposed finger rings 410 mounted thereto. Finger rings 410 accommodate the fingers of the user to facilitate holding and manipulation of the apparatus 400. Handle 402 further includes actuating portion 412 which is mounted to frame 408.

Actuating portion 412 includes a distal inner cylindrical mounting section 414 which is received within an internal bore of frame 408 to mount the actuating portion 412 to frame 408. Mounting section 414 is dimensioned to slide within frame 408 thereby permitting relative movement between the two components, i.e., actuating portion 412 is reciprocally moveable relative to frame 408 to operate the apparatus as will be discussed. Actuating portion 412 further includes a thumb ring structure 415 for accommodating the thumb of the user. A coil spring 417 mounted about mounting section 414 to normally bias the actuating portion 412 to a normal proximalmost position.

The components of handle 402 are preferably fabricated from a suitable rigid polymeric material or a metal such as stainless steel. The supporting components including frame 408 and actuating portion 412 preferably incorporate respective half sections 408a, 412a (FIG. 22) which are secured to each other about their peripheries with the use of adhesives, screws, etc.

Referring now to FIGS. 24–27, in conjunction with FIG. 22, elongate portion 404 is mounted to the distal end of frame 408 through ferrule 416 which is fixedly mounted within corresponding recesses 418 defined in frame 408 (FIG. 22). Elongate portion 404 includes outer delivery catheter 420. Outer delivery tube or catheter 420 is fabricated from a flexible material and has a shape memory portion 422 at its distal end. At its proximal end, delivery tube 420 is fixedly mounted to ferrule 416 by the use of adhesives, crimping, etc . . . . Materials of fabrication for the shape memory portion 422 of delivery catheter 420 include Nitinol. Similar to the aforedescribed embodiment, in the normal unstressed condition of delivery catheter 420, memory portion 422 defines an arcuate orientation angularly oriented relative to the longitudinal axis as shown. In a preferred embodiment (e.g., in BPH application), memory portion 422 defines a radius of curvature "r" ranging between about 0.300 to about 0.500 inches, preferably about 0.400 inches. Delivery catheter 420 preferably has an outer diameter of about 0.48 inches. A Teflon™ shrink tubing 424 is preferably disposed about delivery tube 420 as best depicted in FIG. 27.

Bipolar electrode unit 406 is disposed within delivery catheter 420 and extends through handle 402 where it is connected to actuating portion 412 through ferrule 426. Ferrule 426 is fixedly mounted within a correspondingly dimensioned recess 428 (FIG. 22) formed in actuating portion 412. Through this arrangement, movement of actuating portion 412 causes corresponding translation of electrode unit 406 within delivery catheter 420.

Figures 25, 26:
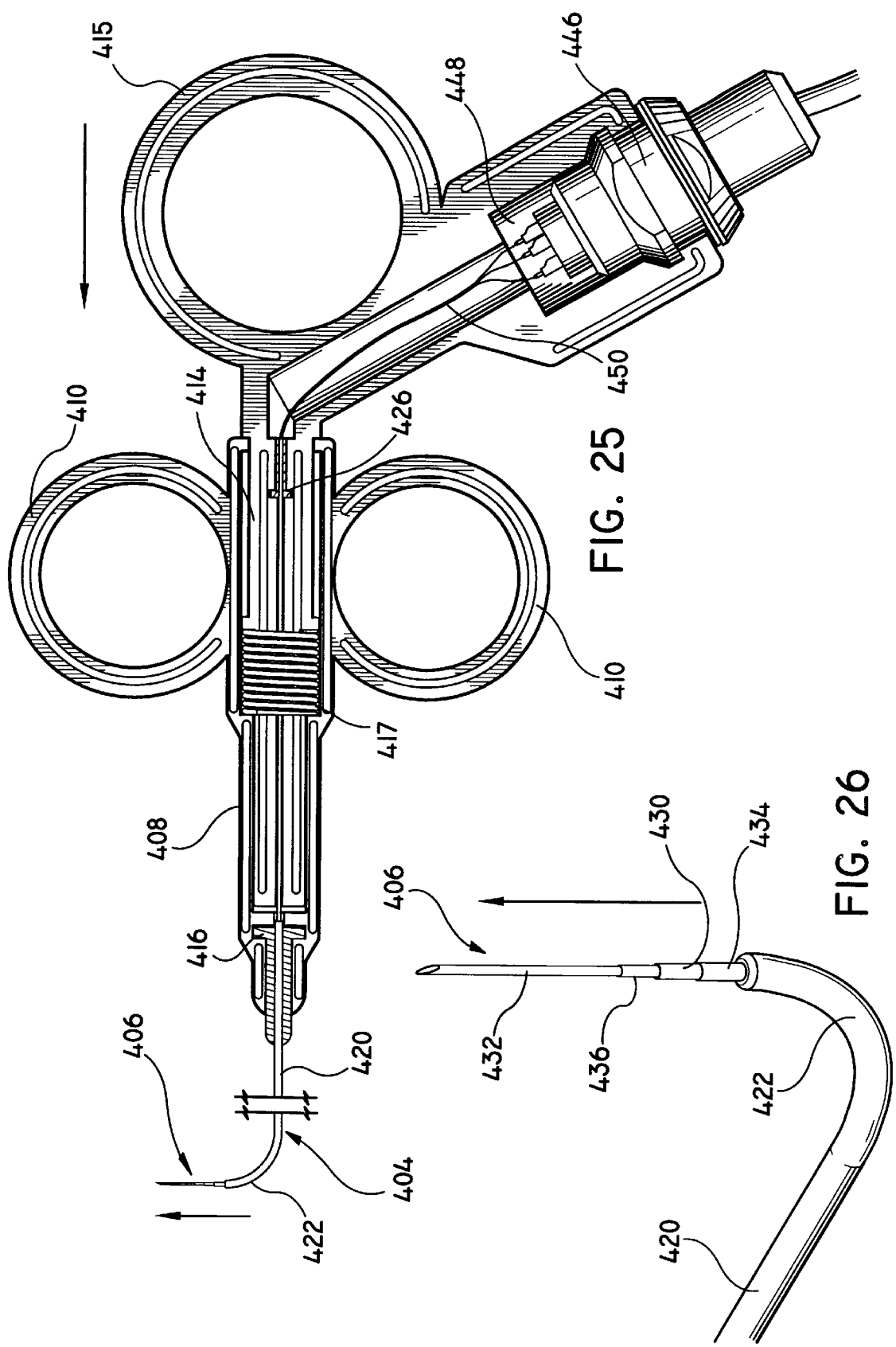
FIG. 25 is a view similar to the view of FIG. 23 illustrating actuation of the actuating portion to deploy the electrode assembly beyond the directional (delivery) tube of the elongate portion.
FIG. 26 is a view similar to the view of FIG. 25 further illustrating the electrode assembly deployed from the directional tube.

As best illustrated in FIGS. 26–27 which depict electrode unit or assembly 406 deployed via advancement of actuating portion 412, the electrode assembly 406 includes an outer tubular bipolar electrode 430 and an inner tubular bipolar electrode 432 coaxially mounted within the outer electrode 430. Inner bipolar electrode 432 extends distally beyond outer tubular electrode 430. Each electrode 430, 432 has insulating layers 434, 436 respectively. Inner electrode 432 is preferably a needle electrode having a sharpened penetrating end as shown.

Figure 30:
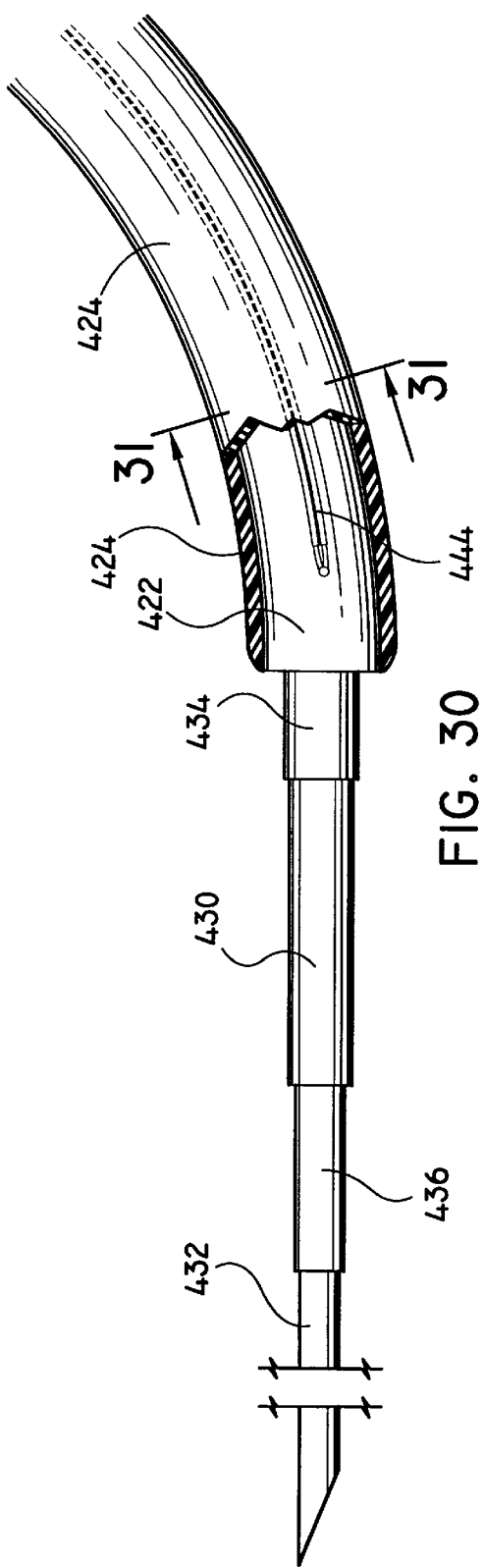
FIG. 30 is a side plan view of the distal end of the directional tube with portions cut away to depict a second thermocouple for detecting the temperature of tissue adjacent the treatment area.
Figure 31:
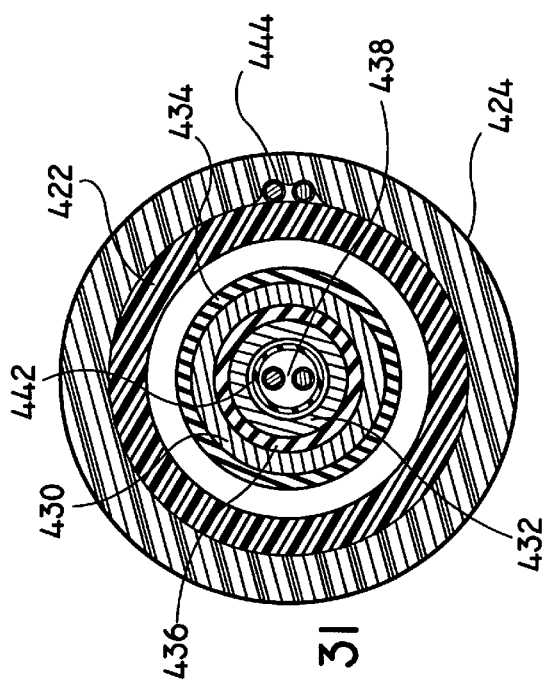
FIG. 31 is a cross-sectional view taken along the lines 31—31 of FIG. 30.

Referring now to FIGS. 27–29, apparatus 400 further includes a first thermocouple 438 which extends within the axial bore of inner electrode 432. First thermocouple 438 is intended to measure the temperature of the tissue within the treatment area for monitoring purposes during the surgical procedure. An epoxy sealant 440 may be applied about the distal end of the thermocouple 438. First thermocouple 438 may be disposed within a protective sleeve 442 as shown. As depicted in FIGS. 30–31, a second thermocouple 444 may also be provided to measure the temperature of the tissue outside and adjacent the treatment area to ensure that this tissue is not undesirably thermally ablated. Second thermocouple 444 preferably extends between delivery catheter 420 and shrink tubing 424 which, as stated above, is wrapped about the outer surface of delivery catheter 420.

With reference again to FIGS. 22, 23 and 25, apparatus 400 further includes an electrical connector 446 which is mounted within a corresponding recess 448 in actuating portion 412 of handle 402. Connector 446 electrically connects the electrode assembly 406 and thermocouples 438, 444 to the RF energy source and the thermocouple accessory instrumentation, respectively, through appropriate wires 450. Accessory instrumentation contemplated for use with thermocouples 438, 444 include a digital monitor to provide a readout of the temperatures ascertained with the thermocouples.

Referring now to FIGS. 32–34, use of the apparatus 400 in connection with the thermal treatment of prostatic tissue to treat BPH will be discussed. Apparatus 400 is intended for use with a conventional scope such as cystoscope 200 which is identical to the cystoscope described hereinabove and is insertable within the working channel 214 of the scope through instrument port 216 (FIG. 13). In a preferred method of application, cystoscope 200 is initially inserted and advanced within the urethral passage "u" whereby the distal end of the scope is positioned adjacent the prostatic tissue to be treated. Auxiliary apparatus 400 is thereafter introduced through channel port 216 and advanced within working channel 214. Alternatively, the apparatus 400 can be inserted through the working channel port 216 and the working channel 214, and the entire assembly inserted into the urethral passage. It is to be noted that memory portion 422 of delivery catheter 420 assumes a generally linear configuration upon insertion within working channel 214 of the scope. Upon exiting the distal end of working channel 214, memory portion 422 assumes its normal unstressed curved orientation depicted in FIGS. 32–34. FIG. 32 illustrates memory portion 422 partially deployed while FIGS. 33–34 illustrate the memory portion 424 in the fully deployed position. As shown in FIG. 34, memory portion 422 will not penetrate the prostatic tissue upon deployment, but, rather will engage the inner wall of the urethra and bias the wall inwardly.

Figures 35, 36:
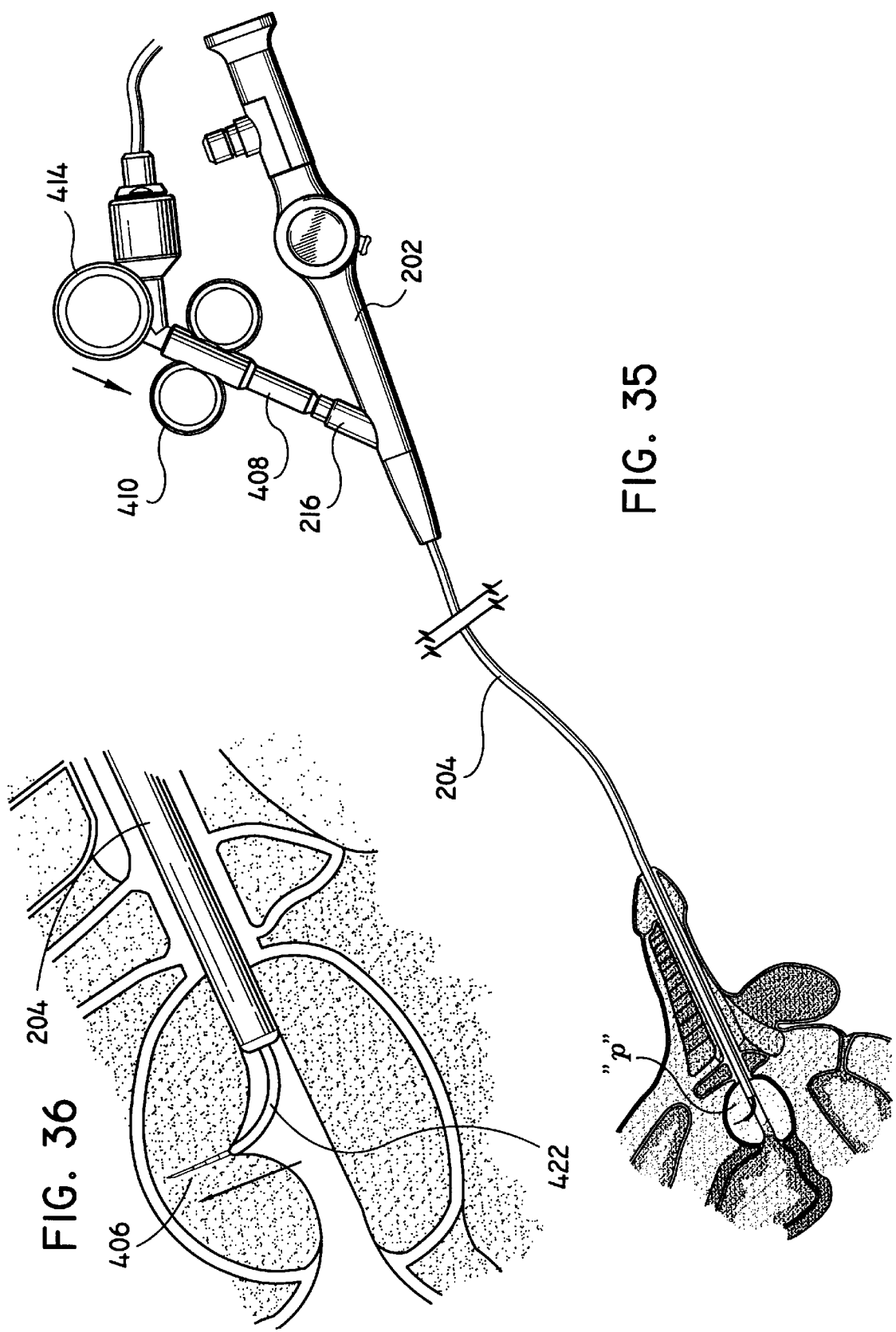
FIG. 35 is a view similar to the view of FIG. 33 illustrating the electrode assembly deployed beyond the directional tube and penetrating the prostatic tissue.
FIG. 36 is an isolated view further illustrating the electrode assembly deployed within the prostatic tissue.

With reference now to FIG. 35–36, actuating portion 412 is then advanced in the direction of the directional arrow of FIG. 35 to advance the electrode assembly 406, i.e., actuating portion 412 is advanced from the position depicted in FIG. 23 to the position depicted in FIG. 25. Upon deployment, the needle portion of inner electrode 432 pierces the urethral wall "u" to access the prostatic tissue "p". Electrode unit 406 is continually advanced whereby outer electrode 430 is disposed within the prostatic tissue and insulating layer 434 of the outer electrode 430 is adjacent the urethral lining. The system is thereafter energized whereby a thermal treatment region is created by transfer of RF energy between the outer and inner electrodes 430, 432.

The coaxial arrangement of the electrode assembly 406 reduces the overall diameter of the elongate portion 404 of the thermal treatment apparatus, thus, facilitating incorporability within a cystoscope. It is to be appreciated that the arrangement and lengths of the exposed electrodes 430, 432 (and thus insulation) may be varied to create other thermal treatment capacities.

FIGS. 37–41 illustrate an alternate embodiment of the auxiliary thermal treatment apparatus of FIG. 20. This apparatus is similar in most respects to the apparatus of FIG. 20, but, incorporates a monopolar electrode assembly having a single monopolar electrode 460 with insulating layer 462. The apparatus may be utilized with a grounding pad positioned adjacent the body as is conventional in the art. Delivery catheter 420 and memory portion 422 are substantially similar to the prior embodiment. A shrink tubing 424 is positioned about delivery catheter 420. As best depicted in FIGS. 40–41, thermocouple 438 is disposed within delivery catheter 420 and thermocouple 444 is disposed between the shrink tubing 424 and the outer surface of delivery catheter 420.

Referring now to FIGS. 42–43, an alternate embodiment of the monopolar thermal treatment apparatus of FIGS. 37–41 is illustrated. Apparatus 500 includes handle portion 502 having frame 504 and actuating portion 506 slidably mounted to the frame. Actuating portion 506 includes dual connectors, namely, electrode connector 508 and infusion port 510. Electrode connector 508 connects to a RF energy source. Infusion port 510 is preferably a luer-type connector and operatively connects to an infusion liquid or dissipating agent utilized to facilitate dissipation of the RF energy at the electrode end. Actuating portion 506 further includes thermocouple connector 512 which connects to one of the thermocouples of the instrument. Frame 504 of handle portion 502 includes a separate thermocouple connector 514 mounted thereto which electrically connects with a second thermocouple incorporated in the instrument. Actuating portion 506 is slidably mounted to frame 504 and is connected to the electrode unit in an identical manner to that described above. The remaining components are identical to their corresponding parts described in connection with the embodiment of FIG. 21. In accordance with this embodiment, other than the hollow passage discussed below, the electrode unit is substantially identical to that described in connection with the aforedescribed embodiment of FIGS. 37–41.

As depicted in FIGS. 45–47, a first thermocouple 516 extends between the outer shrink tubing 518 and delivery catheter 520 and is utilized to measure the temperature of the tissue adjacent the treatment area. First thermocouple 516 is electrically connected to electrode connector 508 of actuating portion 506. A second thermocouple 522 extends between insulating layer 524 and monopolar needle electrode 526 to detect the temperature of the tissue within the treatment area. Second thermocouple 522 is electrically connected to electrode connector 514 of frame 504.

FIGS. 46–47 also illustrate the dissipating agent or fluid 528, e.g., saline solution, which passes through the hollow passage of the electrode 526 as will be discussed.

Figure 44:
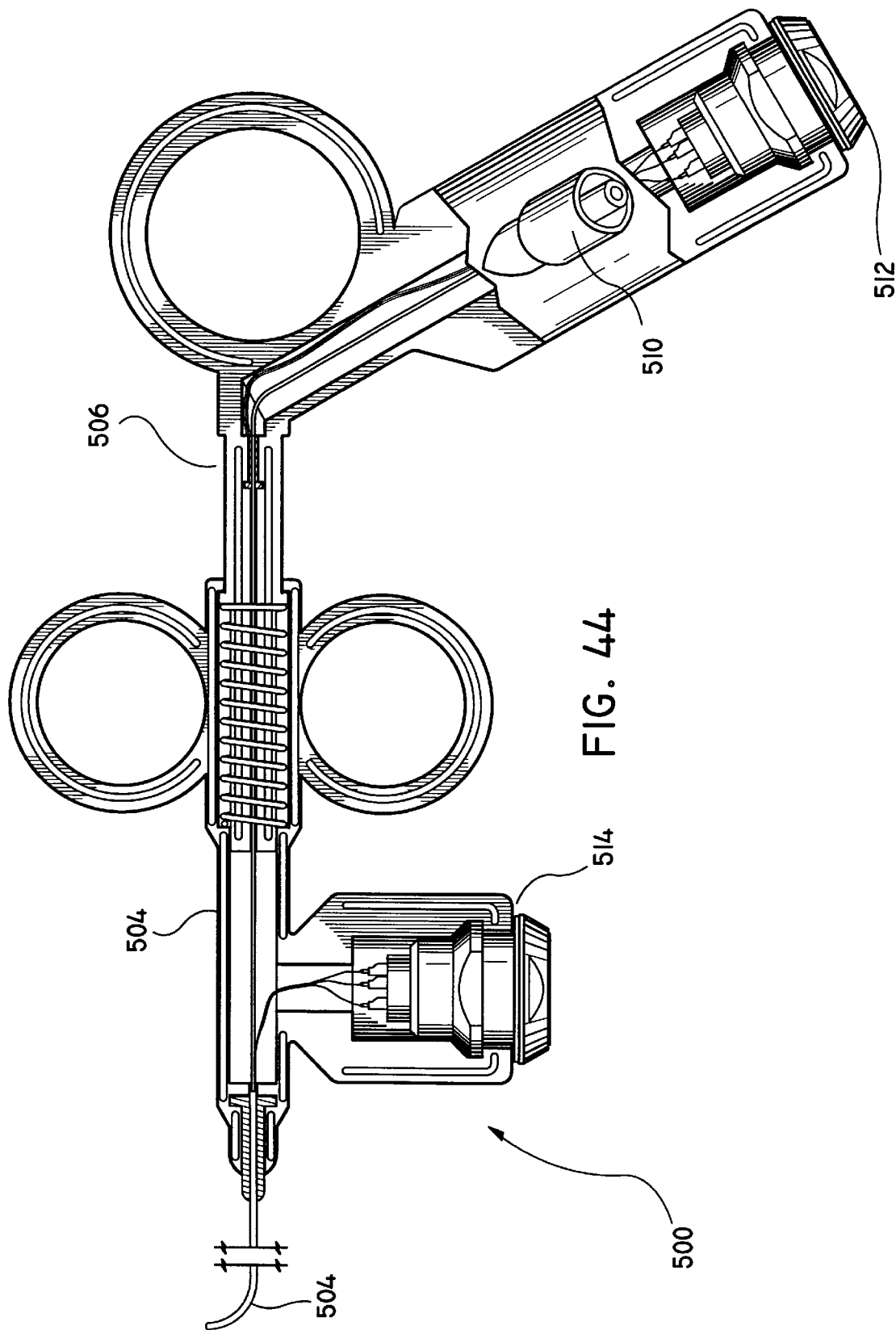
FIG. 44 is a side plan view of the apparatus with the handle in partial cross-section.
Figure 48:
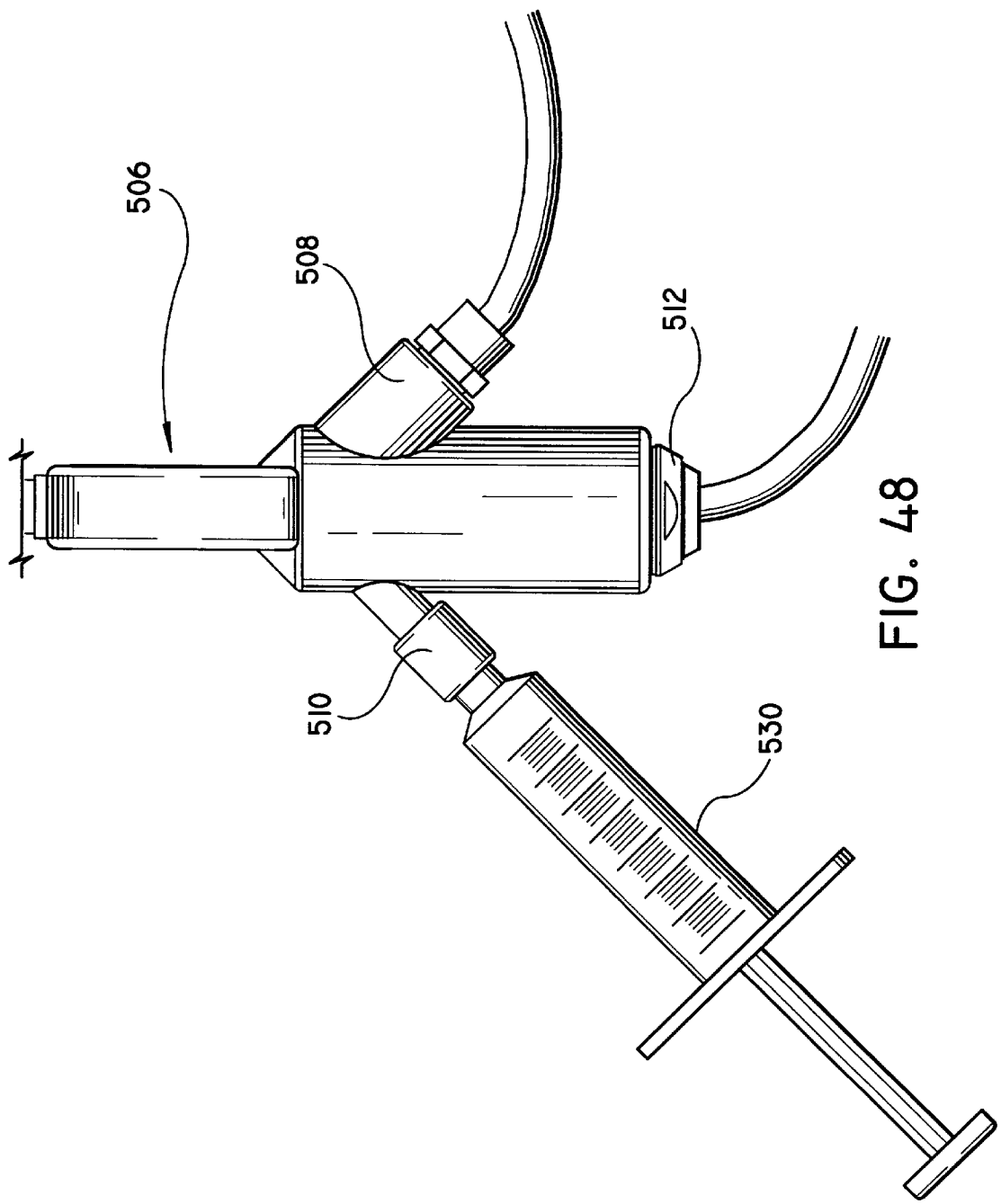
FIG. 48 is a plan view of the handle illustrating a syringe connected to the handle.

With reference now to FIGS. 48–50, use of the apparatus 500 will be described. A syringe 530 containing the dissipating fluid, e.g. hypertonic saline solution, is connected to infusion port 510. In the alternative, a fluid bag may also be utilized and connected to the port in a conventional manner. With the cystoscope 200 accessing the urethral passage, the apparatus 500 is inserted and the needle electrode 526 is deployed by advancing actuating portion 506. Prior to and during treatment, i.e. energiziation of the system to apply RF energy saline solution is infused with syringe 530 through the hollow passage of electrode 526 and into the treatment site to facilitate dissipation of the thermal energy and to assist in focusing the current on the target tissue. Preferably, a tube 532 is provided (FIG. 44) to fluidly connect port 510 and the inner passageway of electrode 526. During treatment, the temperature of the treatment area and area adjacent the treatment area may be monitored with thermocouples 516, 522. Other fluids can be injected through the hollow passage of electrode 526 such as an anesthetic agents or drugs post op to minimize edema.

Port 550 can be provided for suction or irrigation, e.g. injection of isotomic saline in the working channel in the space surrounding the delivery tubes.

It is also envisioned that the auxiliary apparatus described above can be used other than with a scope. For example, the delivery (directing) tubes can be inserted directly into the urethra or other body lumens. The tubes and electrodes can be monitored by ultrasound, MRI, flouroscopy or other imaging techniques. Ultrasound can also be used in conjunction with the endoscope to image the needles in the edenoma.

While the above description contains many specifics, these specifics should not be construed as limitations on the scope of the disclosure, but merely as exemplifications of preferred embodiments thereof. For example, microwave or other forms of electromagnetic energy can be utilized. Those skilled in the art will envision many other possible variations that are within the scope and spirit of the disclosure as defined by the claims appended hereto.

What is claimed is:

1. An apparatus for thermal treatment of tissue, which comprises:
   an elongate portion dimensioned for insertion within a narrow body passage, the elongate portion including:
   a delivery catheter having proximal and distal end portions, and a memory portion at the distal end portion thereof, the memory portion comprised of shape memory material and defining an arcuate configuration when in a normal unstressed condition;
   an electromagnetic probe disposed within and electrically isolated from the delivery catheter and longitudinally moveable relative to and within the delivery catheter between a first position contained within the delivery catheter and a second position wherein at least a probe end portion thereof extends beyond the delivery catheter and within tissue, the electromagnetic probe being adapted to follow the arcuate configuration of the memory portion of the delivery catheter in the normal unstressed condition, the electromagnetic probe including a first outer electrode and a second inner electrode disposed within the outer electrode, the second inner electrode extending beyond the first outer electrode, the probe being connectable to a thermal energy source; and
   a handle portion connected to the elongate portion, the handle portion including a single actuating portion operatively connected to the electromagnetic probe, the actuating portion moveable to move the electromagnetic probe including the first outer electrode and the second inner electrode between the first and second positions.

2. The apparatus according to claim 1, wherein the electromagnetic probe includes a monopolar electrode.

3. The apparatus according to claim 1 including a thermocouple generally disposed adjacent to and operatively cooperating with the electromagnetic probe for detecting temperature of tissue within a treatment area generated by the electromagnetic probe.

4. The apparatus according to claim 3 including a thermocouple generally disposed adjacent to and operatively cooperating with the delivery catheter for detecting temperature of tissue adjacent a treatment area generated by the electromagnetic probe.

5. The apparatus according to claim 1 including a thermocouple generally disposed adjacent to and operatively cooperating with the delivery catheter for detecting temperature of tissue adjacent a treatment area generated by the electromagnetic probe.

6. The apparatus according to claim 1 including a source of dissipating agent operatively connected to the elongate portion for facilitating dissipation of thermal energy at the treatment site and wherein the dissipating agent is distally conveyed through a channel extending through the elongate portion.

7. The apparatus according to claim 6 wherein the electromagnetic probe defines a hollow passageway, the passageway defining the channel for conveyance of the dissipating agent.

8. The apparatus according to claim 1 wherein the elongate portion is dimensioned for insertion within a working channel of a cystoscope.

9. The apparatus according to claim 1 wherein the thermal energy source is a radio frequency (RF) energy source.

10. The apparatus according to claim 9 wherein the first outer electrode and the second inner electrode are configured as bipolar RF electrodes.

11. A system for thermal treatment of tissue, which comprises:
    an endoscope including an elongate body having a working channel;
    an auxiliary thermal treatment device including:
    a handle portion;
    an elongate portion extending distally from the handle portion and being dimensioned for at least partial insertion within the working channel of the endoscope, the elongate portion including:
    at least one delivery member defming a longitudinal axis and having proximal and distal end portions, the delivery member longitudinally moveable within the working channel of the endoscope to extend therebeyond; and
    an electromagnetic probe assembly disposed within the delivery member and longitudinally moveable within the delivery member between an initial position confined within the delivery catheter and an advanced position wherein a probe end portion extends beyond the delivery member and within tissue, the probe assembly including an electrode and an insulating layer coaxially mounted about the electrode, the probe connectable to a thermal energy source;
    a first actuator portion mounted to the handle portion and operatively connected to the delivery member, the first actuator portion moveable relative to the handle portion to move the delivery member such that the distal end portion thereof extends beyond the working channel of the endoscope; and
    a second actuator portion mounted to the handle portion and operatively connected to the electromagnetic probe assembly, the second actuator portion moveable relative to the handle portion to move the electromagnetic probe assembly between the initial position and the advanced position.

12. The system according to claim 11 further comprising a thermal energy source connected to the electromagnetic probe assembly.

13. The system according to claim 11, wherein the delivery member includes a memory portion disposed at the distal end portion thereof, the memory portion comprised of shape memory material and defining a normally unstressed configuration angularly oriented relative to the longitudinal axis and the electromagnetic probe is adapted to follow the normally unstressed configuration of the memory portion.

14. The system according to claim 13, wherein the electromagnetic probe assembly including a first outer electrode and a second inner electrode disposed within the outer electrode, the second inner electrode extending distally beyond the first outer electrode and having a penetrating end portion at a distal end thereof.

15. The system according to claim 14 wherein the first and second electrodes are configured as bipolar RF electrodes.

16. The system according to claim 15 wherein the elongate portion defines a passageway for conveying a dissipating fluid to the operative site to facilitate dissipation of thermal energy generated by the thermal energy source.

17. The system according to claim 16 wherein the second electrode has a channel, the channel being the passageway for conveying the dissipating fluid.

18. An auxiliary electromagnetic thermal treatment apparatus for use with an endoscope to provide the endoscope with electromagnetic thermal treatment capabilities, which comprises:
   a handle portion; and
   an elongate portion extending distally from the handle portion, the elongate portion being dimensioned for at least partial insertion within the working channel of an endoscope, the elongate portion including:
      at least one delivery tube longitudinally moveable relative to the handle portion to extend a portion thereof beyond the working channel of the endoscope; and
      an electromagnetic probe disposed within the delivery tube and defining a probe end portion, the electromagnetic probe longitudinally moveable relative to the delivery tube between an unadvanced position wherein the probe end portion is disposed within the delivery tube and an advanced position wherein the probe end portion extends beyond the delivery tube and within tissue, at least the probe end portion being guided by the delivery tube into the tissue during movement of the electromagnetic probe to the advanced position, the electromagnetic including an electrode and an insulating layer coaxially mounted about the electrode;
   a first actuator mounted to the handle portion and operatively connected to the delivery tube, the first actuator movable to move the delivery tube between a first retracted position and a second deployed position, and
   a second actuator mounted to the handle portion and operatively connected to the electromagnetic probe, the second actuator movable to move the electromagnetic probe between the unadvanced position and the advanced position.

19. The auxiliary apparatus according to claim 18, wherein the delivery tube includes a memory portion comprised of shape memory material and defining a normally unstressed curved configuration, wherein movement of the memory portion beyond the working channel of the endoscope causes the memory portion to assume the normal unstressed curved configuration.

20. The auxiliary apparatus according to claim 19, wherein the electromagnetic probe is adapted to follow the curved configuration of the memory portion of the delivery tube in the normal unstressed condition thereof.

21. The auxiliary apparatus according to claim 20 wherein the elongate portion includes first and second delivery tubes, the first and second delivery tubes each having an electromagnetic probe disposed therein.

22. The auxiliary apparatus according to claim 21 wherein the first and second delivery tubes are connected along respective longitudinal portions thereof.

23. The auxiliary apparatus according to claim 21 wherein the probes are each configured as a bipolar electrode.

24. The auxiliary apparatus according to claim 20 wherein the elongate portion includes a flexible outer sleeve, the one delivery tube being at least partially disposed within the outer sleeve.

25. A system for thermal treatment of tissue, which comprises:
   an endoscope including:
      a frame; and
      an elongated endoscopic portion extending from the frame, the endoscopic portion having a working channel extending along a portion of the length thereof; and
   an auxiliary thermal treatment device including:
      a handle portion;
      an elongate body extending from the handle portion and positionable within the working channel of the endoscopic portion of the endoscope, the elongate body having an axial bore extending at least partially therethrough;
      at least two delivery tubes supported within the elongate body and mounted for movement within the elongate body, each delivery tube having proximal and distal end portions, the distal end portion including a memory portion comprised of a shape memory material and defining a normal curved orientation;
      an electromagnetic probe mounted for reciprocal movement within each delivery tube and defining a probe end portion, the electromagnetic probe movable from a position wherein the probe end portion is confined within the delivery tube to a position wherein the probe end portion extends beyond the delivery tube, the electromagnetic probe including an electrode and an insulating layer coaxially mounted about the electrode;
      a first actuator mounted to the handle portion and operatively connected to the proximal end portions of the delivery tubes, the first actuator actuable to cause movement of the delivery tubes to extend the distal end portions of the delivery tubes beyond the elongate body, to thereby permit the memory portion of each delivery tube to assume their normal curved orientation thereof; and
      a second actuator mounted to the handle portion and operatively connected to the electromagnetic probes, the second actuator actuable to cause movement of the electromagnetic probes to extend the probe end portions beyond the delivery tubes to penetrate tissue, the probe end portions following the path defined by the delivery tubes in the normal curved orientation thereof.

26. The combination of claim 25 wherein the endoscopic portion of the endoscope defines a distal end face and wherein the working channel of the endoscopic portion includes an axial bore extending through the distal end face of the endoscopic portion.

27. The combination of claim 26 wherein the elongate body of the thermal treatment device includes an axial bore extending through the distal end face of the elongate body, the delivery tubes and electromagnetic probes being deployed through the distal end face of the elongate portion.

28. The combination of claim 27 wherein the endoscope includes an optical system for viewing an image of an object.

29. The combination of claim 28 wherein the endoscope includes an illumination system for providing illuminating light.

30. A method for thermally treating tissue, comprising the steps of:

accessing targeted tissue to be thermally treated with an endoscope;

inserting an auxiliary thermal treatment apparatus at least partially into a working channel of the endoscope, the thermal treatment apparatus including a handle portion and an elongate body dimensioned for insertion into the working channel, at least one delivery tube having a memory portion comprised of a shape memory material and movable relative to the handle portion, and an electromagnetic probe disposed within the delivery tube and having a distal end portion and being movable relative to the handle portion, the electromagnetic probe having an electrode and an insulating layer mounted about the electrode;

advancing the delivery tube relative to the handle portion through the elongate body to extend the memory portion of the delivery tube beyond the elongate body and beyond the working channel of the endoscope, whereby the memory portion assumes a normal curved unstressed orientation;

advancing the electromagnetic probe relative to the handle portion and within the delivery tube to extend the distal end portion of the electromagnetic probe confined beyond the delivery tube and into the targeted tissue, whereby the electromagnetic probe follows the path defined by the delivery tube in the normal curved orientation thereof; and supplying electromagnetic energy to the electromagnetic probe to thermally treat the prostatic tissue.

31. The method of claim 30 wherein the step of advancing the delivery tube includes activating a proximally positioned actuator connected to the delivery tube to selectively advance the delivery tube.

32. The method of claim 31 wherein the step of advancing the electromagnetic probe includes activating a proximally positioned actuator connected to the electromagnetic probe to selectively advance the electromagnetic probe.

* * * * *